US010273547B2

(12) United States Patent
Wang et al.

(10) Patent No.: US 10,273,547 B2

(45) Date of Patent: Apr. 30, 2019

(54) MULTIPLEX ASSAY FOR THE DETECTION OF AT LEAST TWO CITRUS PATHOGENS

(71) Applicant: The Regents of the University of California, Oakland, CA (US)

(72) Inventors: Jinbo Wang, Berwyn Heights, MD (US); Tyler Dang, Riverside, CA (US); Georgios Vidalakis, Riverside, CA (US)

(73) Assignee: The Regents of the University of California, Oakland, CA (US)

(*) Notice: Subject to any disclaimer, the term of this patent is extended or adjusted under 35 U.S.C. 154(b) by 472 days.

(21) Appl. No.: 14/905,741

(22) PCT Filed: Jul. 18, 2014

(86) PCT No.: PCT/US2014/047277

§ 371 (c)(1),
(2) Date: Jan. 15, 2016

(87) PCT Pub. No.: WO2015/010075

PCT Pub. Date: Jan. 22, 2015

(65) Prior Publication Data

US 2016/0145678 A1 May 26, 2016

Related U.S. Application Data

(60) Provisional application No. 61/856,589, filed on Jul. 19, 2013.

(51) Int. Cl.

| | |
|---|---|
| ***C12Q 1/68*** | (2018.01) |
| ***C12Q 1/689*** | (2018.01) |
| ***C12Q 1/6895*** | (2018.01) |
| ***C12Q 1/70*** | (2006.01) |

(52) U.S. Cl.

CPC ........... *C12Q 1/689* (2013.01); *C12Q 1/6895* (2013.01); *C12Q 1/701* (2013.01); *C12Q 2600/13* (2013.01); *C12Q 2600/158* (2013.01); *C12Q 2600/16* (2013.01)

(58) Field of Classification Search

CPC ........................................................ C12Q 1/68

See application file for complete search history.

(56) References Cited

U.S. PATENT DOCUMENTS

| | | | |
|---|---|---|---|
| 2006/0046246 | A1 | 3/2006 | Zeng et al. |
| 2011/0105351 | A1 | 5/2011 | Luo et al. |

OTHER PUBLICATIONS

Hocquellet (Detection and identification of the two *Candidatus liberobacter* species associated with citrus huanglongbing by PCR amplification of ribosomal protein genes of the beta operon, Mol Cell Probes. Oct. 1999;13(5):373-9).*

Tsai (Nucleic acid capture assay, a new method for direct quantitation of nucleic acids, Nucleic Acids Res. Mar. 15, 2003; 31(6): e25).*

Hocquellet et al., Detection and identification of the two *Candidatus liberobacter* species associated with citrus huanglongbing by PCR amplification of ribosomal protein genes of the beta operon, Mol Cell Probes. Oct. 1999;13(5):373-9.*

Tomimura et al., Evaluation of genetic diversity among 'Candidatus Liberibacter asiaticus' isolates collected in Southeast Asia, Phytopathology. Sep. 2009;99(9):1062-9. doi: 10.1094/PHYTO-99-9-1062.*

Fujikawa et al., Convenient detection of the citrus greening (huanglongbing) bacterium '*Candidatus liberibacter asiaticus*' by direct PCR from the midrib extract, PLoS One. 2013;8(2):e57011. doi: 10.1371/journal.pone.0057011. Epub Feb. 20, 2013.*

Sankaran et al., Huanglongbing (Citrus Greening) Detection Using Visible, Near Infrared and Thermal Imaging Techniques, Sensors (Basel). 2013; 13(2): 2117-2130. Published online Feb. 6, 2013.*

Li et al., Optimized Quantification of Unculturable *Candidatus liberibacter* Spp. in Host Plants Using Real-Time PCR, Plant Disease , Jun. 2008, vol. 92, No. 6 pp. 854-861.*

Bushnell et al., "ProbeDesigner: for the design of probesets for branched DNA (bDNA) signal amplification assays," *Bioinformatics*, vol. 15, No. 5, 1999, pp. 348-355.

Hocquellet et al., "Detection and identification of the two *Candidatus liberobacter* species associated with citrus huanglongbing by PCR amplification of ribosomal protein genes of theβ operon," *Molecular and Cellular Probes*, vol. 13, Issue 5, Oct. 1999, pp. 373-379.

Kawabe et al., "Quantification of DNA of citrus huanglongbing pathogen in diseased leaves using competitive PCR," Bacterial and Phytoplasma Diseases, *Journal of General Plant Pathology* Dec. 2006, vol. 72, Issue 6, pp. 355-359.

International Search Report dated Nov. 3, 2014 in PCT/US2014/047277, 18 pages.

* cited by examiner

*Primary Examiner* — Aaron A Priest

(74) *Attorney, Agent, or Firm* — Kilpatrick Townsend & Stockton LLP

(57) ABSTRACT

The present invention provides methods and compositions for detecting multiple citrus pathogens using a multiplex branched DNA signal amplification reaction.

28 Claims, 2 Drawing Sheets

Specification includes a Sequence Listing.

MULTIPLEX ASSAY FOR THE DETECTION OF AT LEAST TWO CITRUS PATHOGENS

CROSS-REFERENCE TO RELATED APPLICATIONS

This application a National Stage of International Appl. No. PCT/US2014/047277, filed Jul. 18, 2014, which claims priority benefit of U.S. provisional application No. 61/856,589, filed Jul. 19, 2013, each of which applications is herein incorporated by reference for all purposes.

STATEMENT AS TO RIGHTS TO INVENTIONS MADE UNDER FEDERALLY SPONSORED RESEARCH AND DEVELOPMENT

This invention was made with Government support under Grant No. 58-5302-1-119 and 59-5302-1-226, awarded by the USDA-ARS (Agricultural Research Services). The Government has certain rights in this invention.

REFERENCE TO SEQUENCE LISTING

This application includes a Sequence Listing as a text file named "81906-970122-seq.txt" created Jan. 15, 2016, and containing 48,934 bytes. The material contained in this text file is incorporated by reference in its entirety for all purposes.

BACKGROUND OF THE INVENTION

Citrus is susceptible to numerous disease caused by plant pathogens. There is a need for efficient and sensitive methods of detecting pathogens.

The method of the present invention provides a method for the detection of multiple, e.g., at least two or at least five, citrus pathogens in a single sample using a multiplex branched signal amplification reaction. The present invention thus provides an accurate, efficient, and quick method of detecting multiple citrus pathogens that is also suitable for high throughput screenings.

BRIEF SUMMARY OF THE INVENTION

The present invention provides methods and kits for detecting at least two citrus DNA pathogen/disease targets where the pathogens are HLB (Huanglongbing, citrus greening, *Candidatus Liberibacter asiaticus*) and canker (*Xanthomonas axonopodis* pv. *citri*). In some embodiments, the methods and kits additionally comprise components for detecting a housekeeping citrus gene, e.g., NADH dehydrogenase gene (Nad5) as an internal control.

Provided herein are specific probes for each of the at two pathogen targets, and methods for detecting the two citrus pathogens and a citrus control gene in a plant sample.

In a further aspect, the present invention provides methods and kits for detecting at least five citrus DNA pathogen/disease targets where the pathogens HLB (Huanglongbing, citrus greening, *Candidatus Liberibacter asiaticus*), witches' broom (*Candidatus Phytoplasma aurantifolia*), citrus canker (*Xanthomonas axonopodis* pv. *citri*), CVC (Citrus Variegated Chlorosis, *Xylella fastidiosa* subspecies *pauca*), and citrus stubborn disease (*Spiroplasma citri*). In some embodiments, the methods and kits additionally comprise components for detecting a housekeeping citrus gene, e.g., NADH dehydrogenase gene (Nad5) (*Citrus sinensis*) as an internal control.

Provided herein are specific probes for each pathogen target, and methods for detecting the five citrus pathogens and a citrus control gene in a plant sample.

The methods described herein can be coupled to a procedure for high throughput robotic extraction and purification of nucleic acid targets, optimized for citrus tissues. The methods are user friendly and can be applied for the detection of endemic and/or exotic plant pathogens in quarantine or certification program. Furthermore, the methods can be adopted by monitoring services of plant health status and disease management programs around the world.

DETAILED DESCRIPTION OF THE INVENTION

Figure 1:
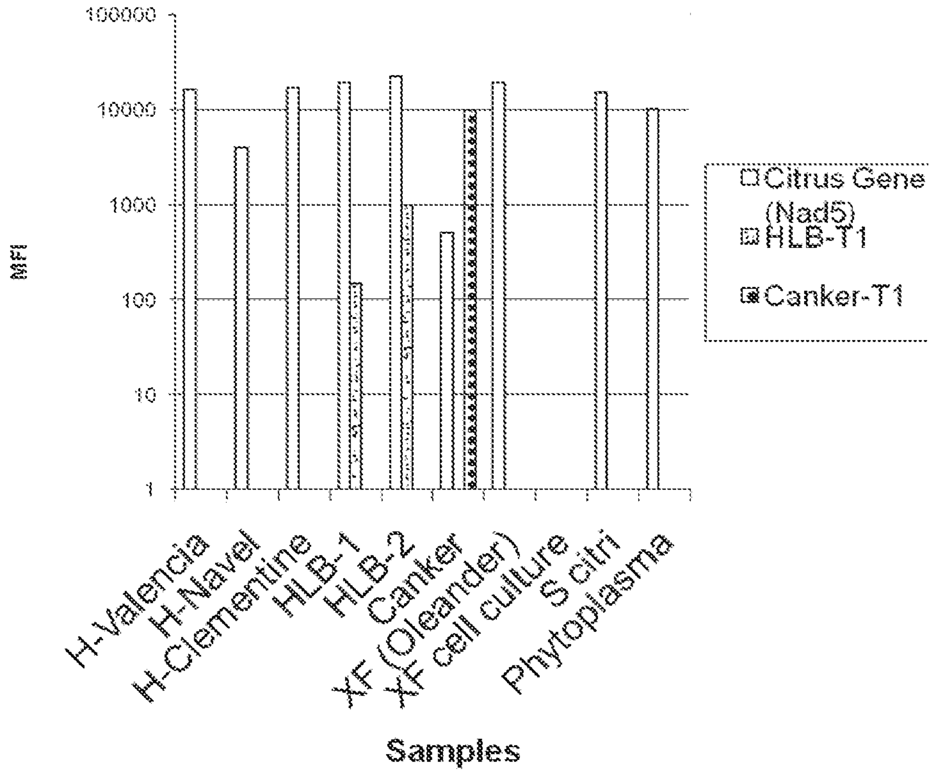
FIG. 1 provides illustrative data showing a 3-Plex reaction detecting citrus pathogens.

As used herein, a "probe that targets a pathogen" refers to a nucleotide sequence that hybridizes to a desired region of a target nucleic acid in the pathogen.

The term "hybridization" refers to the formation of a duplex structure by two single stranded nucleic acids due to complementary base pairing. Hybridization can occur between exactly complementary nucleic acid strands or between nucleic acid strands that contain minor regions of mismatch. As used herein, the term "substantially complementary" refers to sequences that are complementary except for minor regions of mismatch. Typically, the total number of mismatched nucleotides over a hybridizing region is not more than 3 nucleotides for sequences about 15 nucleotides in length.

The term "probe" refers to an oligonucleotide that selectively hybridizes to a target nucleic acid under suitable conditions. A hybridization assay carried out using a probe under sufficiently stringent hybridization conditions enables the selective detection of a specific target sequence comprising the region of interest of a pathogen nucleic acid. The probe hybridizing region is preferably from about 10 to about 35 nucleotides in length. In some embodiments, the probe hybridizing region is 15 to about 35 nucleotides in length. The use of modified bases or base analogues which affect the hybridization stability, which are well known in the art, may enable the use of shorter or longer probes with comparable stability. The term "nucleotide" thus encompasses naturally occurring nucleotides and nucleotide analogs.

The term "target sequence" or "target region" refers to a region of a nucleic acid in a pathogen of interest to which a probe to the pathogen binds.

A "capture extender probe" or "CE probe" as used here is a polynucleotide that is capable of hybridizing to a nucleic acid of interest from a citrus pathogen and to a capture probe. The capture extender probe has a first polynucleotide sequence that is complementary to a capture probe, and a second polynucleotide sequence, e.g., a sequence as shown in Table 1, which is complementary to a citrus pathogen nucleic acid as described herein. The capture probe is typically immobilized to a solid support, including but not limited to a chip (e.g., an array), well, bead, or other solid support or matrix.

A "label extender probe" or "LE" as used here is a polynucleotide that is capable of hybridizing to a nucleic acid of interest from a pathogen and to a label probe system. The label extender probe has a first polynucleotide sequence that is complementary to a polynucleotide sequence of the label probe system and a second polynucleotide sequence, e.g., a sequence as shown in Table 1, which is complementary to a citrus pathogen as described herein. The signal-amplifying probe in the present invention typically comprises branched DNA, e.g., may include a pre-Amplifier probe, an Amplifier probe, and a Label probe.

Introduction

The present invention provides methods to diagnose infection with citrus pathogens. In some embodiments, the methods can be used in high-throughput screenings of thousands of plant samples in regulatory and research programs. Branched DNA technology (bDNA) employs a sandwich nucleic acid hybridization assay for nucleic acid detection and quantification that amplifies the reporter signal rather than the target sequence of interest that is to be detected. Thus, bDNA technology amplifies signal directly from captured target DNA without purification or reverse transcription. DNA quantitation is performed directly from a tissue sample. By measuring the nucleic acid at the sample source, the assay avoids variations or errors inherent to extraction and amplification of target polynucleotides. The QuantiGene Plex technology can be combined with multiplex bead based assay system such as the Luminex system described below to enable simultaneous detection of multiple pathogens of interest.

In brief in an assay of the invention, a target nucleic acid to be detected is released from cells and captured by a Capture Probe (CP) on a solid surface (e.g., a well of a microtiter plate) through synthetic oligonucleotide probes called Capture Extenders (CEs). Each capture extender has a first polynucleotide sequence that can hybridize to the target nucleic acid and a second polynucleotide sequence that can hybridize to the capture probe. Typically, two or more capture extenders are used. Probes of another type, called Label Extenders (LEs), hybridize to different sequences on the target nucleic acid and to sequences on an amplification multimer. Additionally, Blocking Probes (BLs), which hybridize to regions of the target nucleic acid not occupied by CEs or LEs, are typically used to reduce non-specific target probe binding. A probe set for a given nucleic acid thus has CEs, LEs, and typically BLs for the target citrus pathogen. The CEs, LEs, and BLs are complementary to nonoverlapping sequences in the target nucleic acid from the citrus pathogen, and are typically, but not necessarily, contiguous.

Signal amplification begins with the binding of the LEs to the target DNA. An amplification multimer is then typically hybridized to the LEs. The amplification multimer has multiple copies of a sequence that is complementary to a label probe (it is worth noting that the amplification multimer is typically, but not necessarily, a branched-chain nucleic acid; for example, the amplification multimer can be a branched, forked, or comb-like nucleic acid or a linear nucleic acid). A label, for example, alkaline phosphatase, is covalently attached to each label probe. Alternatively, the label can be noncovalently bound to the label probes. In the final step, labeled complexes are detected, e.g., by the alkaline phosphatase-mediated degradation of a chemilumigenic substrate, e.g., dioxetane. Luminescence is reported as relative light unit (RLUs) on a microplate reader. The amount of chemiluminescence is proportional to the level of DNA in the sample.

The present invention provides a method and compositions for detecting the presence or absence of at least one or two of the citrus pathogens described herein. As explained above, detection is performed using bDNA signal amplification technology and capture extender probes and label extender probes that target the pathogen nucleic acid regions described herein. The general design of branched amplification assays, e.g., suitable amplification multimers, considerations in designing capture probes that bind to the capture extenders, etc.; configuration; and hybridization conditions for such reactions can be determined using methods known in the art (see, e.g., U.S. Patent Application Publication No. 20120003648 and the references cited therein).

Citrus Pathogen Probes

Probes to the five pathogen targets and exemplar internal citrus gene were developed based on specific genomic sequences and characteristics in the pathogens' genome. The probes (Table 1) included Capture Extenders (CE), Label Extenders (LE), Blocking Probes (BL) as per manufacturer's recommendations were designed and developed based on the conserved sequences in the genome of each pathogen. Probes for HLB, Witches' broom, citrus canker, CVC, citrus stubborn disease, and Nad5 were based on target sequence alignment from data deposited in GenBank.

The present invention employs CE and LE probes that comprise sequences presented in Table 1 or are variants of the sequences in Table 1 that retain the ability to hybridize to the same target nucleic acid sequence as the probes shown in Table 1 such that the presence of the pathogen in a plant sample can be detected. Such variant probe sequences typically have no more than 1, 2, 3, 4, 5, 6, 7, or 8 nucleotide changes relative to a probe sequence as shown in Table 1. In some embodiments, a variant probe useful in the invention comprises at least 7, 8, 9, 10, 11, 12, 13, 14, 15, 16, 17, 18, 19, or 20, or more, contiguous nucleotides of a sequence shown in Table 1.

The methods and compositions for detecting single or multiple citrus pathogens as described herein may also include probes to detect a control nucleic acid sequence. In some embodiments, the control is a housekeeping gene that is common to citrus plants. In some embodiments, the housekeeping gene is NADH dehydrogenase gene (abbreviated herein as NAD). In some embodiments, the CE and LE probes comprises the NAD sequences shown in Table 1 or are variants of the sequences that retain the ability to hybridize to the target region in the NAD sequence. In some embodiments, such a variant probe comprises at least 7, 8, 9, 10, 11, 12, 13, 14, 15, 16, 17, 18, 19, or 20, or more, contiguous nucleotides of a sequence shown in Table 1; or has no more than 1, 2, 3, 4, 5, 6, 7, or 8 nucleotide changes relative to the sequence shown in Table 1.

In some embodiments, one or more blocking probes may be employed. Table 1 provides examples of sequences that may be employed in block probes useful in the invention.

In some embodiments, multiple capture extender and/or label extender probes shown in Table 1, or variants thereof as described herein, are used in the invention. In some embodiments, each of the probes that target a pathogen is shown in Table 1. In some embodiments, all of the capture extender and label extender probes shown in Table 1 for a given pathogen, or variants as described herein, are used in the methods, kits, and reactions of the invention for detecting the pathogen. In some embodiments, all of the probes, including any blocking probes, shown in Table 1, or variants thereof as described herein, for a given pathogen are used in the methods, kits, and reactions of the invention. Thus for example, in some embodiments of the invention, all of the probes shown in Table 1 to detect the presence or absence of HLB are used in the invention. In some embodiments, all of the probes shown in Table 1 to detect the presence or absence of Witches' broom are used in the invention. In some embodiments, all of the probes shown in Table 1 to detect the presence or absence of citrus canker are used in the invention. In some embodiments, all of the probes shown in Table 1 to detect the presence or absence of CVC are used in the invention. In some embodiments, all of the probes shown in Table 1 to detect the presence or absence of citrus stubborn disease are used in the invention. In some embodiments, the invention employs all of the probes shown in Table 1 for detecting the presence or absence of HLB, all of the probes shown in Table 1 for detecting the presence or absence of witches' broom, all of the probes shown in Table 1 for detecting the presence or absence of citrus canker, all of the probes shown in Table 1 for detecting the presence or absence of CVC, and all of the probes shown in Table 1 for detecting the presence of absence of citrus stubborn disease in a single reaction mixture. In some embodiments, the invention further employs all of the probes shown in Table 1 to detect the presence of the housekeeping gene NAD. In some embodiments, the invention provides methods, reaction mixtures, and kits that comprise all of the pathogen probes shown in Table 1 and all of the probes shown in Table 1 for detecting the control.

Plant Samples

The sample evaluated for the presence of citrus pathogens can be from any plant material (e.g., seed, foliage, limbs, trunk, bark, rootstock, fruit, germplasm, propagule, cuttings, and budwood). DNA is extracted using well-known techniques. Such a DNA sample may also comprise RNA. Methods for extracting DNA from a plant samples are known to those skilled in the art and are described in Bilgin et al., *Nature Protocols,* 4:333-340, (2009); Berendzen et al., *Plant Methods,* 1:4 (2005); Elspeth MacRae, *Methods in Molecular Biology*, vol. 353*: Protocols for Nucleic Acid Analysis by Nonradioactive Probes, Second Edition*, Humana Press, New Jersey, 15-24, (2007). Non-limiting examples of commercially available plant DNA extraction kits include DNAeasy Plant Mini Kit (Qiagen, Hilden, Germany), PrepEase DNA Isolation Kit (Affymetrix, Santa Clara, Calif.), PureLink® Genomic Plant DNA Purification Kit (Life Technologies, Carlsbad, Calif.), and Plant/Fungi DNA Isolation kit (Sigma-Aldrich, St. Louis, Mo.).

The following examples are offered to illustrate, but not to limit, the claimed invention.

EXAMPLES

High Throughput Assays for Rapid and Accurate 3-Plex Detection of Citrus Pathogens The need to detect and identify multiple plant pathogens simultaneously has led development and adaptation of a new molecular approach for disease diagnosis. Multiplex QuantiGene (Afftmetrix/Panonmics) and Lumninex RNA assays for reliable detection of citrus pathogens were developed. The sequential hybridization-based assay utilizes Luminex magnetic beads and branched DNA (bDNA) signal amplification. A Luminex 200 instrument was used for the read out of fluorescence resulting from positive sequence-specific hybridizations from beads in the flow cytometer. The assay was performed using 96-well plates which allows for direct detection and quantitation of up to 36 RNA or 34 DNA targets per well in one simultaneous assay.

Example 1 provides an illustrative assay with a total of three targets for the simultaneous detection, identification, and quantification for two citrus DNA pathogens/disease (carrying DNA genomes) and one housekeeping citrus gene internal control: HLB (Huanglongbing, citrus greening, *Candidatus Liberibacter asiaticus*) and citrus canker (*Xanthomonas axonopodis* pv. *citri*); and an internal control, NADH dehydrogenase gene (Nad5).

Example 2 provides an illustrative assay with a total of eight targets for the simultaneous detection, identification, and quantification for five citrus DNA pathogens/disease (carrying DNA genomes) and one housekeeping citrus gene internal control: HLB (Huanglongbing, citrus greening, *Candidatus Liberibacter asiaticus*), Witches' broom (*Candidatus Phytoplasma aurantifolia*), citrus canker (*Xanthomonas axonopodis* pv. *citri*), CVC (Citrus Variegated Chlorosis, *Xylella fastidiosa* subspecies *pauca*), and an internal control, Nad5.

Sequences of specific probes including Capture Extenders (CE), Label Extenders (LE), Blocking Probes (BL) were designed and developed for the specific detection of the citrus pathogen targets and a housekeeping citrus gene as an internal control with QuantiGene Plex and Luminex based DNA assay (see, Table 1).

TABLE 1

Capture Extenders (CE), Label Extenders (LE), Blocking Probes (BL) for HLB, Witches' broom, Citrus canker, CVC, citrus stubborn disease, and a housekeeping citrus gene as an internal control (SEQ ID NOS: 1-167).

| Targets[a] | Probes | Probe Sequence (5'→3') |
|---|---|---|
| HLB (1) | HLB 001 CE | tcgcaagattaaaactcaaagga |
| | HLB 002 CE | ggattagataccctggtagtccac |
| | HLB 003 CE | agtgtagaggtgaaattcgtagatattc |
| | HLB 004 CE | cggcgattaagttagaggtgaaat |
| | HLB 005 CE | gcgtaaagggcgcgtagg |
| | HLB 006 CE | agcgttgttcggaataactag |
| | HLB 007 LE | tccgcctggggagtacgg |
| | HLB 008 LE | cgcacgtaacgcattaagcac |
| | HLB 009 LE | tgggtggtttaccattcagtgg |
| | HLB 010 LE | gctgtaaacgatgagtgctagctgt |
| | HLB 011 LE | aaagcgtggggagcaaaca |
| | HLB 012 LE | gatactgacgctgaggcgcg |
| | HLB 013 LE | aaggcggctcactggcct |
| | HLB 014 LE | ggaggaacaccggtggcg |
| | HLB 015 LE | ggagaggtgagtggaattccg |
| | HLB 016 LE | gcctttaatactgattgtctagagttca |
| | HLB 017 LE | cttcgtgccagcagccg |

TABLE 1-continued

Capture Extenders (CE), Label Extenders (LE), Blocking Probes (BL) for HLB, Witches' broom, Citrus canker, CVC, citrus stubborn disease, and a housekeeping citrus gene as an internal control (SEQ ID NOS: 1-167).

| Targets[a] | Probes | Probe Sequence (5'→3') |
|---|---|---|
| | HLB 018 LE | gagaagaagccccggctaa |
| | HLB 019 BL | cccaggctcaaccttggaact |
| HLB (2) | HLB 001 CE | ctcctgtgggttatagagattacca |
| | HLB 002 CE | tctcgtctttacccgaacaaaa |
| | HLB 003 CE | tctccctcactcaattcaagttca |
| | HLB 004 CE | cagttgttttacgctcaccctc |
| | HLB 005 CE | gctatacctacagaaccagcgct |
| | HLB 006 LE | tttgaaatcttttcactagattctttaat |
| | HLB 007 LE | ggcctttcaccagaaaagaaatat |
| | HLB 008 LE | cctctttgcaaaatctcgattaat |
| | HLB 009 LE | tgatcaatcagatactcaatatccactat |
| | HLB 010 LE | ccgctttacatataaaggagaacct |
| | HLB 011 LE | ttgatcattcccctcaatttctat |
| | HLB 012 LE | gctcaatcatggaataattaattgga |
| | HLB 013 LE | gccatgatacgacgcttagcac |
| | HLB 014 LE | tgacttcagaaaaataacccgtg |
| | HLB 015 LE | tgctggcaattgcgaaatat |
| | HLB 016 BL | cgccgaattacagaatcatacga |
| | HLB 017 BL | agaatcacataatcggatacatcatt |
| Witches' Broom | Witches' Broom 001 CE | cgcattttaccgctacacatg |
| | Witches' Broom 002 CE | tcgggtatcttcgaattaaacaa |
| | Witches' Broom 003 CE | catgtcaagacctggtaaggtttt |
| | Witches' Broom 004 CE | gcagtctcgttaaagtcccca |
| | Witches' Broom 005 CE | gcatgatgatttgacgtgatcc |
| | Witches' Broom 006 CE | ttgtacccaggtcataaggg |
| | Witches' Broom 007 LE | cctctggtgttcctccatatattta |
| | Witches' Broom 008 LE | ccagcaagccgcctacg |
| | Witches' Broom 009 LE | gtgcctcagcgtcagtaaagac |
| | Witches' Broom 010 LE | gtttgctccccacgctttc |
| | Witches' Broom 011 LE | tggactaccagggtatctaatcct |
| | Witches' Broom 012 LE | cttagtactcatcgtttacggcg |
| | Witches' Broom 013 LE | cagtaccggtttaacccgaca |
| | Witches' Broom 014 LE | ggcggagtacttaatgtgttaactt |
| | Witches' Broom 015 LE | tttcatacttgcgtacgtactactca |
| | Witches' Broom 016 LE | ggagtcccgtcaattcattaag |
| | Witches' Broom 017 LE | ccactatattactatagcttcgcaaaaa |
| | Witches' Broom 018 LE | caccacctgtgtttctgataacct |
| | Witches' Broom 019 BL | catgatccaccgcttgtgc |
| | Witches' Broom 020 BL | acgagctgacgacaaccatg |
| | Witches' Broom 021 BL | ttaggacttaacctacatctcacga |
| | Witches' Broom 022 BL | gataagggttgcgctcgtt |
| | Witches' Broom 023 BL | ccataacgtgctggcaactaa |
| | Witches' Broom 024 BL | tcaccttcctccaatttatcattg |
| Canker | Canker 001 CE | gctgaccatgccgcatgtg |
| | Canker 002 CE | cggcgacttcgactatctgc |
| | Canker 003 CE | ctggagtgccacctggtctc |
| | Canker 004 CE | ccggcgatatcttcgaaga |
| | Canker 005 CE | ccgcactacctcaaggcca |
| | Canker 006 CE | ggcgccatcaccggct |
| | Canker 007 CE | cctgtcgaccacgccgt |
| | Canker 008 LE | tggaagaggtcaaggagacgc |
| | Canker 009 LE | cgtgaatccaagagctatatcgtga |
| | Canker 010 LE | gagatggcgtcctaccgca |
| | Canker 011 LE | tcaaggcgcgcatcagc |
| | Canker 012 LE | gctaaagctgcccaacgtg |
| | Canker 013 LE | attccgccgcgccgc |
| | Canker 014 LE | agatcagcctggcctacaaat |
| | Canker 015 LE | gcctgctggtgttcgtgg |
| | Canker 016 LE | acggctggagcgcgac |
| | Canker 017 LE | gcaccgagcgcgtgcg |
| | Canker 018 LE | tgggcgagcgggtcgg |
| | Canker 019 LE | ggcggatttcgtttaccgaac |
| | Canker 020 LE | cgcatcctgcagcaggagg |
| | Canker 021 LE | agatcgaccgcaagatcctg |
| | Canker 022 BL | agttgctcggcagcacctt |
| | Canker 023 BL | cttacgcgcggctggac |
| CVC (1) | CVC 001 CE | caatccctgatgtttgtgcaga |
| | CVC 002 CE | gtttgcaatctgtatctgtttctga |
| | CVC 003 CE | gcttcaaacgctgcaaagtttc |

TABLE 1-continued

Capture Extenders (CE), Label Extenders (LE), Blocking Probes (BL) for HLB, Witches' broom, Citrus canker, CVC, citrus stubborn disease, and a housekeeping citrus gene as an internal control (SEQ ID NOS: 1-167).

| Targets[a] | Probes | Probe Sequence (5'→3') |
|---|---|---|
| | CVC 004 CE | tccagtacagtggattcctgttg |
| | CVC 005 CE | ttcccttaagattgttgcaac |
| | CVC 006 CE | ctgagacttgacaatctgggtagc |
| | CYC 007 LE | gttgacccatcgacaatccc |
| | CVC 008 LE | tagcacttgcgcttgagctt |
| | CVC 009 LE | tttgtgccaattcacgttgc |
| | CVC 010 LE | acataacgcgcatcctctaact |
| | CVC 011 LE | tttgatttggagggtgccc |
| | CVC 012 LE | cctgcatctggctcgtgtaa |
| | CVC 013 LE | catgatagcttgacgttgcattg |
| | CVC 014 LE | aaacaaccgaaagcgcacc |
| | CVC 015 LE | cacgattccatcaattgggg |
| | CVC 016 BL | cgagtcgcaatctcaatttcga |
| | CVC 017 BL | tgagcaatagaccgtcgcgt |
| | CVC 018 BL | cctgctccagttgcgcca |
| | CVC 019 BL | acgagcctcagtttctaccttt |
| CVC (2) | CVC 001 CE | tgcatccactacaggcaatttt |
| | CVC 002 CE | cgattgcgattggtactacgg |
| | CVC 003 CE | ggttccaaaacggatgggaat |
| | CVC 004 CE | gcattgctaccatgaatggct |
| | CVC 005 CE | acttattctatgcgcctaggca |
| | CVC 006 CE | aaacctggttcttggtgggtc |
| | CVC 007 LE | cattgacatcaattgccaatgg |
| | CVC 008 LE | gcgatagcgataggtaatggag |
| | CVC 009 LE | gccatcggttcaggcaa |
| | CVC 010 LE | cggctggcatagattcgatt |
| | CVC 011 LE | ggctagtcgatatttctggtgca |
| | CVC 012 LE | cttatatgtcaatgagggtaaactcg |
| | CVC 013 LE | cagagtattccctgttttatgattatag |
| | CVC 014 LE | caagccagatttcacgcaaa |
| | CVC 015 LE | cattcatagtgcttctaacgataaatg |
| | CVC 016 LE | gctcaagtctatgtaaattccgactc |
| | CVC 017 LE | ggcgacagtagtcagacatcctt |
| | CVC 018 LE | gactgaaaattgcgtagaaatactg |
| | CVC 019 BL | gcgatttctatagggaccgg |
| | CVC 020 BL | cccgttcgcaatctcaagat |
| | CVC 021 BL | tagcacaggggctgcgtt |
| | CVC 022 BL | accagcggcgccactg |
| Citrus stubborn disease | Stubborn 001 CE | ttgtctgacaattcaacaacatattta |
| | Stubborn 002 CE | aaataaacattgttggtatgacctaag |
| | Stubborn 003 CE | ctttttctttcttttcgtttatttgt |
| | Stubborn 004 CE | ttcgctcatatttcaaactgtttg |
| | Stubborn 005 CE | aagttgactatcacttgctagttgct |
| | Stubborn 006 CE | ctgtctttgatttgcaaggtaa |
| | Stubborn 007 LE | aaccatcaagtttttatcccgttt |
| | Stubborn 008 LE | cctttgattgttgccagttgtg |
| | Stubborn 009 LE | ggatattgtcgtatccatttgct |
| | Stubborn 010 LE | tgtttaattgactagcactatacccac |
| | Stubborn 011 LE | cgatcagcaacagcactcgc |
| | Stubborn 012 LE | tgacagtttaccattggttttaacc |
| | Stubborn 013 LE | ttgtcaacggttcggttgc |
| | Stubborn 014 LE | taactgctcgacaacttgctctt |
| | Stubborn 015 LE | cgcttggaatttgcgtttt |
| | Stubborn 016 LE | ttggtatttaccttatcattttgatat |
| | Stubborn 017 LE | atttaacagtaatgtttactttgtcattt |
| | Stubborn 018 LE | attgttctgatgtcgcattattgt |
| | Stubborn 019 BL | ccattatcagtatttcaatattcttttattt |
| | Stubborn 020 BL | gtcaatttttactatctgcaaaaagat |
| | Stubborn 021 BL | aacgaaactttatctttctcataattg |
| | Stubborn 022 BL | ggtttaaactcactttggtttaaaaca |
| Nad5 | Nad 001 CE | ggctatatgatctttgcttgcg |
| | Nad 002 CE | cgttttcatgatagcaaggtgct |
| | Nad 003 CE | ccccttttatttgaatacccaccta |
| | Nad 004 CE | gatgctatggagggtcccact |
| | Nad 005 CE | ggattgcatacttggtcaccc |
| | Nad 006 CE | caatatgagatttaatgccataactctt |
| | Nad 007 CE | cccagaaattcttggatttcttg |
| | Nad 008 LE | tagcttattcaacttgcagtcaatta |
| | Nad 009 LE | tctttcacttaatgaatcacgcg |
| | Nad 010 LE | ttacagaacgatctaaagagggtca |

TABLE 1-continued

Capture Extenders (CE), Label Extenders (LE), Blocking Probes (BL) for HLB, Witches' broom, Citrus canker, CVC, citrus stubborn disease, and a housekeeping citrus gene as an internal control (SEQ ID NOS: 1-167).

| Targets[a] | Probes | Probe Sequence (5'→3') |
|---|---|---|
| | Nad 011 LE | tgcggcaaccactggaata |
| | Nad 012 LE | caggagctacgacgtcattcct |
| | Nad 013 LE | tttcgggccgtttttaqctctc |
| | Nad 014 LE | gcatctctaactattcggttagcg |
| | Nad 015 LE | gcagctactatggtaacagctgg |
| | Nad 016 LE | ccagtatccgcttcgattcat |
| | Nad 017 LE | tttcaaacagtagacttttcaacca |
| | Nad 018 LE | gttgggaaatcggcacagat |
| | Nad 019 LE | atttgtatttacttttattggtgct |
| | Nad 020 BL | cggctttgattgttattacttctg |
| | Nad 021 BL | tttttgctcgtgctagtgcc |

[a]HLB (Huanglongbing, citrus greening, *Candidatus Liberibacter asiaticus*), Witches' broom (*Candidatus Phytoplasma aurantifolia*), citrus canker (*Xanthomonas axonopodis* pv. citri), CVC (Citrus Variegated Chlorosis, *Xylella fastidiosa* subspecies pauca), citrus stubborn disease (*Spiroplasma citri*), and a housekeeping citrus gene, NADH dehydrogenase gene (Nad5) as an internal control The procedure from the QuantiGene Plex DNA Assay User Manual from Affymetrix/Panomics Inc. is provided below.

Capturing Target DNA from Purified DNA or Total Nucleic Acid

1. Sample and reagent preparation: thaw probe set, blocking reagent and nucleic acid samples (both RNA and DNA or DNA only), and place them on ice.
2. Prepare 2.5 M NaOH solution.
3. Pre-warm lysis mixture at 37° C. for 30 minutes.
4. Prepare sample and a working bead mix including nuclease-free water, lysis mixture, blocking reagent, capture beads, probe set, according to reaction composition (Table 2).
5. Vortex working bead mix for 30 sec, transfer 20 μl to each well of the hybridization plate.
6. Add 80 μl prepared nucleic acid samples (or DNA sample) to each well of the above plate.
7. Seal the hybridization plate with a pressure seal and mount the plate into the shaking incubator.
8. Incubate for 18-22 hours at 54° C. at 600 rpm.
9.

TABLE 2

Working Bead Mix Set Up

| Order of addition | Reagent | Per well (μl) |
|---|---|---|
| 1 | Sample | 40 |
| 2 | Lysis mixture | 18 |
| 3 | Probe set | 5 |
| 4 | 2.5M NaOH solution | 5 |
| | Room temperature 30 minutes | |
| 5 | Neutralization Buffer | 12 |
| Sample subtotal | | 80 |
| 1 | Nuclease-free water | 1.8 |
| 2 | Lysis mixture | 15 |
| 3 | Blocking reagent | 2 |
| 4 | Proteinase K | 0.2 |
| 5 | Capture beads | 1 |
| Working bead mix subtotal | | 20 |
| Total | | 100 |

Signal Amplification and Detection of DNA Targets

1. Place label probe diluent and SAPE diluent to room temperature. Incubate amplifier diluent at 37° C. for 20 minutes.
2. Prepare 200 ml wash buffer including 0.6 ml wash buffer Component 1, 10 ml wash buffer Component 2 and 189.4 ml nuclease-free water.
3. Add 36 μl pre-amplifier to 12 ml amplifier diluent.
4. Take the hybridization plate out of the shaking incubator, and spin at 240 g for 60 seconds.
5. Open the pressure seal, mix with pipette, then transfer the hybridization mixture to the magnetic separation plate.
6. Put the magnetic separation plate on the plate holder of the plate washer for 60 seconds, then empty the magnetic separation and wash three times with 100 μl wash buffer.
7. Add 100 μl pre-amplifier solution to each well.
8. Seal the magnetic separation plate with a foil plate seal and shake for 60 minutes at 50° C. with 600 rpm.
9. Add 36 μl amplifier to 12 ml amplifier diluent.
10. Take the magnetic separation plate out of the shaking incubator.
11. Open the foil plate seal.
12. Put the magnetic separation plate on the plate holder of the plate washer for 60 seconds, then empty the magnetic separation plate and wash three times with 100 μl wash buffer.
13. Add 100 μl amplifier solution to each well.
14. Seal the magnetic separation plate with a foil plate seal and shake for 60 minutes at 50° C. with 600 rpm.
15. Add 36 μl label probe to 12 ml label probe diluent.
16. Take the magnetic separation plate out of the shaking incubator and open the foil plate seal.
17. Put the magnetic separation plate on the plate holder of the plate washer for 60 seconds, then empty the magnetic separation plate and wash three times with 100 μl wash buffer.
18. Add 100 μl label probe solution to each well.
19. Seal the magnetic separation plate with a foil plate seal and shake for 60 minutes at 50° C. with 600 rpm.
20. Add 36 μl SAPE to 12 ml SAPE diluent.
21. Take the magnetic separation plate out of the shaking incubator and open the foil plate seal.

22. Put the magnetic separation plate on the plate holder of the plate washer for 60 seconds, then empty the magnetic separation plate and wash three times with 100 µl wash buffer.
23. Add 100 µl SAPE solution to each well.
24. Seal the magnetic separation plate with a foil plate seal and shake for 30 minutes at 50° C. with 600 rpm.
25. Take the magnetic separation plate out of the shaking incubator, open the foil plate seal.
26. Put the magnetic separation plate on the plate holder of the plate washer for 60 seconds, then empty the magnetic separation plate and wash three times with 100 µl SAPE wash buffer.
27. Add 130 µl SAPE wash buffer to each well.
28. Seal the magnetic separation plate with a foil plate seal and cover the magnetic separation plate with foil and shake for 2-3 minutes at room temperature with 600 rpm, then use Luminex instrument to read.

Example 1. High Throughput DNA Assays for Rapid and Accurate 3-Plex Detection of Citrus Pathogens The assay was performed using samples from healthy and infected citrus plants with HLB, canker, *Xylella fastidiosa* (XF), stubborn (*Spiroplasma citri*), Witches' broom (*Candidatus Phytoplasma aurantifolia*), respectively (FIG. 1) and cell culture of XF. A procedure for high throughput robotic extraction and purification of nucleic acid targets, optimized for citrus tissues, was developed and used with the Luminex-based QuantiGene Plex system to increase uniformity and cost effectiveness of the test. Samples HLB-1 and HLB-2 were detected to show specific positive reactions with HLB, but not other pathogen targets. In addition, samples HLB-1 and HLB-2 were detected to show positive reactions with Nad5, the positive internal control for citrus plants, which could be used to access the DNA extraction quality and to normalize data for accurate quantification of the pathogen populations among samples. Similarly, sample canker was detected to show specific positive reactions with Nad5 and canker, but not other DNA pathogen targets. Finally, the healthy Navel, Valencia sweet orange and Clementine samples showed positive reaction with Nad5 only, but not to any pathogen targets. These data showed that the assay is capable of specific detection of each target including Nad5, HLB and canker.

Sensitivity studies using serial dilutions of different samples, respectively, suggested that those samples, obtained by the high throughput robotic extraction and purification of nucleic acid targets or crude extraction of total nucleic acid, were consistently detected after dilution of up to 100 times or more, respectively.

Figure 2:
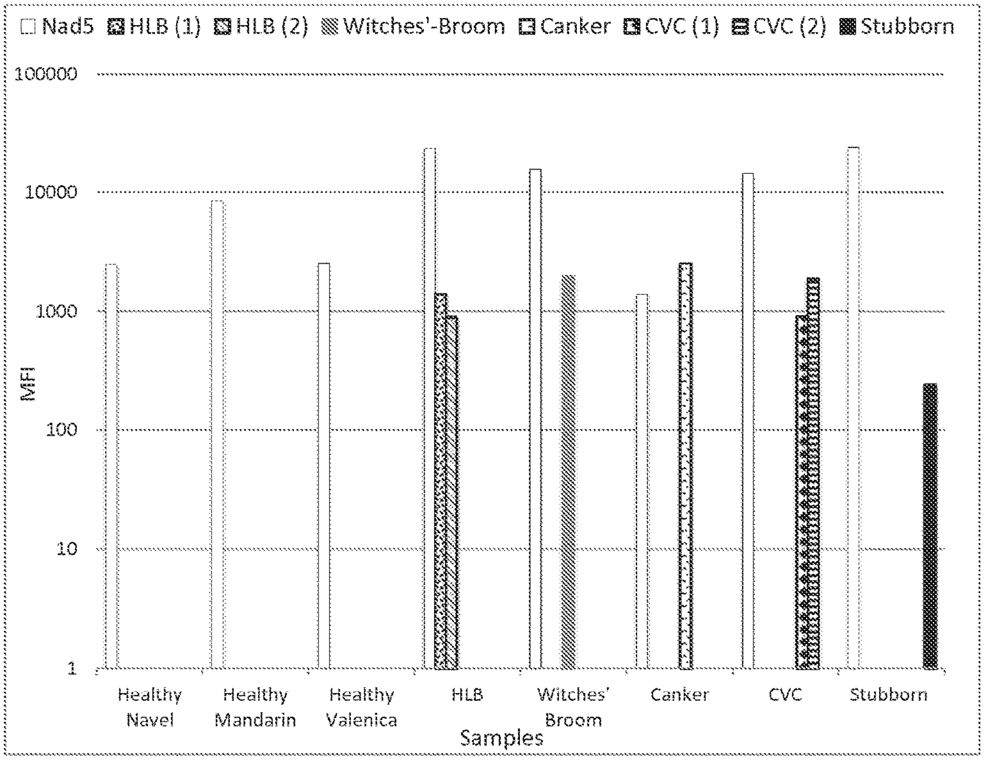
FIG. 2 illustrates the capability of an 8-Plex assay to detect citrus pathogens.

Example 2. High Throughput DNA Assays for Rapid and Accurate 8-Plex Detection of Citrus Pathogens This example illustrates that the 8-plex assay can detect 5 citrus pathogens (HLB, Witches' broom, Citrus canker, CVC, citrus stubborn disease) and a citrus housekeeping gene Nad5. The 8-plex assay employs two sets of probes each to detect HLB and CVC, while Witches' broom, citrus canker, and citrus stubborn each employs one set of probes. FIG. 2 illustrates the specificity of the HLB, Witches' broom, citrus canker, CVC, citrus stubborn, and Nad5 probes to its respective targets.

The assay was performed using samples from healthy and infected citrus plants with Huanglongbing, Witches' broom, Citrus canker, CVC, Citrus-stubborn disease, respectively, (FIG. 2). A procedure for high throughput robotic extraction and purification of nucleic acid targets, optimized for citrus tissues, was developed and used with the Luminex-based QuantiGene Plex system to increase uniformity and cost effectiveness of the test. Samples HLB-1 and HLB-2 were detected to show specific positive reactions with HLB, but not other pathogen targets. In addition, samples HLB-1 and HLB-2 were detected to show positive reactions with Nad5, the positive internal control for citrus plants, which could be used to access the DNA extraction quality and to normalize data for accurate quantification of the pathogen populations among samples. Similarly, Witches' broom, citrus canker, CVC, and stubborn samples showed specific positive reactions with Nad5 and their respective targets, but not other DNA pathogen targets. Finally, the healthy Navel sweet orange, mandarin, and Valencia sweet orange variety samples showed positive reaction with Nad5 only and not to any pathogen targets. These data demonstrated that the assay can specifically detect of each target: Nad5, Huanglongbing, Witches' broom, citrus canker, CVC, and citrus stubborn.

Sensitivity studies using serial dilutions of different samples, respectively, suggested that those samples, obtained by the high throughput robotic extraction and purification of nucleic acid targets or crude extraction of total nucleic acid, were consistently detected after dilution of up to 100 times or more, respectively.

All publications, patents, accession numbers, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A reaction mixture comprising:

(a) probes for detecting the presence or absence of at least two citrus pathogens, wherein the at least two citrus pathogens are Huanglongbing (HLB) and Citrus Variegated Chlorosis (CVC); and further wherein the reaction mixture comprises at least one capture extender probe and label extender probe selected from a first set of detection probes as follows:

(i) a capture extender probe and a label extender probe that targets HLB, wherein:

the capture extender probe that targets HLB comprises at least 8, 9, or 10 contiguous nucleotides of a probe sequence of any one of SEQ ID NOS:1-6; and the label extender probe that targets the HLB comprises at least 8, 9, or 10 contiguous nucleotides of a probe sequence of any one of SEQ ID NOS:7-18; or the capture extender probe that targets HLB comprises at least 8, 9, or 10 contiguous nucleotides of a probe sequence of any one of SEQ ID NOS:20-24; and the label extender probe that targets HLB comprises at least 8, 9, or 10 contiguous nucleotides of a probe sequence of any one of SEQ ID NOS:25-34; and (ii) a capture extender probe a label extender probe that targets CVC, wherein:

the capture extender probe that targets CVC comprises at least 8, 9, or 10 contiguous nucleotides of a probe sequence of any one of SEQ ID NOS:84-89; and the label extender probe that targets CVC comprises at least 8, 9, or 10 contiguous nucleotides of a probe sequence of any one of SEQ ID NOS:90-98; or the capture extender probe that targets CVC comprises at least 8, 9, or 10 contiguous nucleotides of a probe sequence of any one of SEQ ID NOS:103-108; and the label extender probe that targets CVC comprises at least 8, 9, or 10 contiguous nucleotides of a probe sequence of any one of SEQ ID NOS:109-120;

and (b) a capture probe immobilized on a solid support that hybridizes to one or more of the capture extender probes.

2. The reaction mixture of claim 1, comprising multiple capture extender probes and multiple label extender probes that target the at least two pathogens, wherein the multiple capture extender probes and multiple label extender probes are selected from the first set of detection probes.

3. The reaction mixture of claim 1, further comprising at least one capture extender probe and at least one label extender probe that target a pathogen selected from a Witches' broom pathogen, a citrus canker pathogen, and a citrus stubborn pathogen.

4. The reaction mixture of claim 3, wherein the at least one capture extender probe and at least one label extender probe that target the Witches' broom pathogen, the citrus canker pathogen, or the citrus stubborn pathogen is selected from the second set of detection probes as follows:

a capture extender probe that targets a Witches' Broom pathogen and comprises at least 8, 9, or 10 contiguous nucleotides of a probe sequence of any one of SEQ ID NOS:37-42; and a label extender probe that targets the Witches' Broom pathogen and comprises at least 8, 9, or 10 contiguous nucleotides of a probe sequence of any one of SEQ ID NOS:43-54;

a capture extender probe that targets a citrus canker pathogen and comprises at least 8, 9, or 10 contiguous nucleotides of a probe sequence of any one of SEQ ID NOS:61-67; and a label extender probe that targets the citrus canker pathogen and comprises at least 8, 9, or 10 contiguous nucleotides of a probe sequence of any one of SEQ ID NOS:68-81; and a capture extender probe that targets a citrus stubborn disease pathogen and comprises at least 8, 9, or 10 contiguous nucleotides of a probe sequence of any one of SEQ ID NOS: 125-130; and a label extender probe that targets the Citrus stubborn disease pathogen and comprises at least 8, 9, or 10 contiguous nucleotides of a probe sequence of any one of SEQ ID NOS: 131-142.

5. The reaction mixture of claim 4, comprising multiple capture extender probes and multiple label extender probes that target the Witches' broom pathogen, the citrus canker pathogen, or the citrus stubborn pathogen, wherein the multiple capture extender probes and multiple label extender probes are selected from the set of second detection probes.

6. The reaction mixture of claim 1, further comprising at least one capture extender probe and at least one label extender probe that target each of the following three pathogens: a Witches' broom pathogen, a citrus canker pathogen, and a citrus stubborn pathogen.

7. The reaction mixture of claim 6, wherein the at least one capture extender probe and at least one label extender probe that target the three pathogens is each selected from a second set of detection probes as follows:

a capture extender probe that targets a Witches' Broom pathogen and comprises at least 8, 9, or 10 contiguous nucleotides of a probe sequence of any one of SEQ ID NOS:37-42; and a label extender probe that targets the Witches' Broom pathogen and comprises at least 8, 9, or 10 contiguous nucleotides of a probe sequence of any one of SEQ ID NOS:43-54;

a capture extender probe that targets a citrus canker pathogen and comprises at least 8, 9, or 10 contiguous nucleotides of a probe sequence of any one of SEQ ID NOS:61-67; and a label extender probe that targets the citrus canker pathogen and comprises at least 8, 9, or 10 contiguous nucleotides of a probe sequence of any one of SEQ ID NOS:68-81; and a capture extender probe that targets a citrus stubborn disease pathogen and comprises at least 8, 9, or 10 contiguous nucleotides of a probe sequence of any one of SEQ ID NOS: 125-130; and a label extender probe that targets the Citrus stubborn disease pathogen and comprises at least 8, 9, or 10 contiguous nucleotides of a probe sequence of any one of SEQ ID NOS: 131-142.

8. The reaction mixture of claim 7, comprising multiple capture extender probes and multiple label extender probes that target the Witches' broom pathogen, the citrus canker pathogen, and the citrus stubborn pathogen, wherein the multiple capture extender probes and multiple label extender probes are selected from the set of second detection probes.

9. The reaction mixture of claim 1, further comprising one or more blocking probes for the at least two pathogens, wherein the one or more blocking probes comprise 8, 9, or 10 contiguous nucleotides of a probe sequence of any one of SEQ ID NOS:19, 35, 36, 99, 100, 101, 102, 121, 122, 123, and 124.

10. The reaction mixture of claim 7, further comprising multiple blocking probes that comprise at least 8, 9, or 10 contiguous nucleotides of a probe sequence of any one of SEQ ID NOS:19, 35, 36, 55, 56, 57, 58, 59, 60, 82, 83, 99, 100, 101, 102, 121, 122, 123, 124, 143, 144, 145, or 146.

11. The reaction mixture of claim 1, further comprising a capture extender probe and a label extender probe for Nad5, wherein the capture extender probe for Nad5 comprises at least 8, 9, or 10 contiguous nucleotides of a probe sequence of any one of SEQ ID NOS:147-153; and the label extender probe for Nad5 comprises at least 8, 9, or 10 contiguous nucleotide of a probe sequence of any one of SEQ ID NOS:154-165.

12. The reaction mixture of claim 11, comprising multiple capture extender probes to Nad5, each comprising at least 8, 9, or 10 contiguous nucleotides of a probe sequence of any one of SEQ ID NOS: 147-153; and multiple label extender probes for Nad5 each comprising at least 8, 9, or 10 contiguous nucleotide of a probe sequence of any one of SEQ ID NOS: 154-165.

13. The reaction mixture of claim 11, further comprising a blocking probe comprising at least 8, 9, or 10 contiguous nucleotides of SEQ ID NO:166; and/or at least 8, 9, or 10 contiguous nucleotides of SEQ ID NO:167.

14. A kit comprising:

(a) probes for detecting the presence or absence of at least two citrus pathogens, wherein the at least two citrus pathogens are Huanglongbing (HLB) and Citrus Variegated Chlorosis (CVC); and further wherein the reaction mixture comprises at least one capture extender probe and label extender probe selected from a first set of detection probes as follows:

(i) a capture extender probe and a label extender probe that targets HLB, wherein:

the capture extender probe that targets HLB comprises at least 8, 9, or 10 contiguous nucleotides of a probe sequence of any one of SEQ ID NOS:1-6; and the label extender probe that targets the HLB comprises at least 8, 9, or 10 contiguous nucleotides of a probe sequence of any one of SEQ ID NOS:7-18; or the capture extender probe that targets HLB comprises at least 8, 9, or 10 contiguous nucleotides of a probe sequence of any one of SEQ ID NOS:20-24; and the label extender probe that targets HLB comprises at least 8, 9, or 10 contiguous nucleotides of a probe sequence of any one of SEQ ID NOS:25-34; and (ii) a capture extender probe a label extender probe that targets CVC, wherein:

the capture extender probe that targets CVC comprises at least 8, 9, or 10 contiguous nucleotides of a probe sequence of any one of SEQ ID NOS:84-89; and the label extender probe that targets CVC comprises at least 8, 9, or 10 contiguous nucleotides of a probe sequence of any one of SEQ ID NOS:90-98; or the capture extender probe that targets CVC comprises at least 8, 9, or 10 contiguous nucleotides of a probe sequence of any one of SEQ ID NOS:103-108; and the label extender probe that targets CVC comprises at least 8, 9, or 10 contiguous nucleotides of a probe sequence of any one of SEQ ID NOS:109-120;

and (b) a capture probe immobilized on a solid support that hybridizes to one or more of the capture extender probes.

15. The kit of claim 14, comprising multiple capture extender probes and multiple label extender probes that target the at least two pathogens, wherein the multiple capture extender probes and multiple label extender probes are selected from the first set of detection probes.

16. The kit of claim 14, further comprising at least one capture extender probe and at least one label extender probe that target a pathogen selected from a Witches' broom pathogen, a citrus canker pathogen, and a citrus stubborn pathogen.

17. The reaction mixture of claim 16, wherein the at least one capture extender probe and at least one label extender probe that target the Witches' broom pathogen, the citrus canker pathogen, or the citrus stubborn pathogen is selected from a second set of detection probes as follows:

a capture extender probe that targets a Witches' Broom pathogen and comprises at least 8, 9, or 10 contiguous nucleotides of a probe sequence of any one of SEQ ID NOS:37-42; and a label extender probe that targets the Witches' Broom pathogen and comprises at least 8, 9, or 10 contiguous nucleotides of a probe sequence of any one of SEQ ID NOS:43-54;

a capture extender probe that targets a citrus canker pathogen and comprises at least 8, 9, or 10 contiguous nucleotides of a probe sequence of any one of SEQ ID NOS:61-67; and a label extender probe that targets the citrus canker pathogen and comprises at least 8, 9, or 10 contiguous nucleotides of a probe sequence of any one of SEQ ID NOS:68-81; and a capture extender probe that targets a citrus stubborn disease pathogen and comprises at least 8, 9, or 10 contiguous nucleotides of a probe sequence of any one of SEQ ID NOS: 125-130; and a label extender probe that targets the Citrus stubborn disease pathogen and comprises at least 8, 9, or 10 contiguous nucleotides of a probe sequence of any one of SEQ ID NOS: 131-142.

18. The kit of claim 17, comprising multiple capture extender probes and multiple label extender probes that target the Witches' broom pathogen, the citrus canker pathogen, or the citrus stubborn pathogen, wherein the multiple capture extender probes and multiple label extender probes are selected from the set of second detection probes.

19. The kit of claim 14, further comprising at least one capture extender probe and at least one label extender probe that target each of the following three pathogens: a Witches' broom pathogen, a citrus canker pathogen, and a citrus stubborn pathogen.

20. The kit of claim 19, wherein the at least one capture extender probe and at least one label extender probe that target the three pathogens is each selected from a second set of detection probes as follows:

a capture extender probe that targets a Witches' Broom pathogen and comprises at least 8, 9, or 10 contiguous nucleotides of a probe sequence of any one of SEQ ID NOS:37-42; and a label extender probe that targets the Witches' Broom pathogen and comprises at least 8, 9, or 10 contiguous nucleotides of a probe sequence of any one of SEQ ID NOS:43-54;

a capture extender probe that targets a citrus canker pathogen and comprises at least 8, 9, or 10 contiguous nucleotides of a probe sequence of any one of SEQ ID NOS:61-67; and a label extender probe that targets the citrus canker pathogen and comprises at least 8, 9, or 10 contiguous nucleotides of a probe sequence of any one of SEQ ID NOS:68-81; and a capture extender probe that targets a citrus stubborn disease pathogen and comprises at least 8, 9, or 10 contiguous nucleotides of a probe sequence of any one of SEQ ID NOS: 125-130; and a label extender probe that targets the Citrus stubborn disease pathogen and comprises at least 8, 9, or 10 contiguous nucleotides of a probe sequence of any one of SEQ ID NOS: 131-142.

21. The kit of claim 20, comprising multiple capture extender probes and multiple label extender probes that target the Witches' broom pathogen, the citrus canker pathogen, and the citrus stubborn pathogen, wherein the multiple capture extender probes and multiple label extender probes are selected from the set of second detection probes.

22. The kit of claim 14, further comprising one or more blocking probes for the at least two pathogens, wherein the one or more blocking probes comprise 8, 9, or 10 contiguous nucleotides of a probe sequence of any one of SEQ ID NOS:19, 35, 36, 99, 100, 101, 102, 121, 122, 123, and 124.

23. The kit of claim 19, further comprising multiple blocking probes that comprise at least 8, 9, or 10 contiguous nucleotides of a probe sequence of any one of SEQ ID NOS:19, 35, 36, 55, 56, 57, 58, 59, 60, 82, 83, 99, 100, 101, 102, 121, 122, 123, 124, 143, 144, 145, or 146.

24. The kit of claim 14, further comprising a capture extender probe and a label extender probe for Nad5, wherein the capture extender probe for Nad5 comprises at least 8, 9, or 10 contiguous nucleotides of a probe sequence of any one of SEQ ID NOS:147-153; and the label extender probe for Nad5 comprises at least 8, 9, or 10 contiguous nucleotide of a probe sequence of any one of SEQ ID NOS:154-165.

25. The kit of claim 24, comprising multiple capture extender probes to Nad5, each comprising at least 8, 9, or 10 contiguous nucleotides of a probe sequence of any one of SEQ ID NOS: 147-153; and multiple label extender probes for Nad5 each comprising at least 8, 9, or 10 contiguous nucleotide of a probe sequence of any one of SEQ ID NOS: 154-165.

26. The kit of claim 25, further comprising a blocking probe comprising at least 8, 9, or 10 contiguous nucleotides of SEQ ID NO:166; and/or at least 8, 9, or 10 contiguous nucleotides of SEQ ID NO:167.

27. A method of detecting the presence or absence at least two citrus pathogens, wherein the at least two citrus pathogens are Huanglongbing and Citrus Variegated Chlorosis (CVC) in a plant sample, the method comprising:

extracting DNA from said sample;

performing a multiplex branched DNA signal amplification reaction; wherein the reaction comprises a reaction mixture of claim 1; and detecting the presence or absence of a signal above background, wherein the presence of the signal is indicative of the presence of the pathogen in the plants sample.

28. A method of detecting the presence or absence at least two citrus pathogens, wherein the at least two citrus pathogens are Huanglongbing and Citrus Variegated Chlorosis (CVC) in a plant sample, the method comprising:

extracting DNA from said sample;

performing a multiplex branched DNA signal amplification reaction with capture extender and label extender probes of a kit of claim 14.

* * * * *

SEQUENCE LISTING

```
<160> NUMBER OF SEQ ID NOS: 167

<210> SEQ ID NO 1
<211> LENGTH: 23
<212> TYPE: DNA
<213> ORGANISM: Artificial Sequence
<220> FEATURE:
<223> OTHER INFORMATION: synthetic HLB(1) target capture extender probe
      HLB 001 CE for Candidatus Liberibacter asiaticus (Huanglongbing
      (HLB), citrus greening)
```

<400> SEQUENCE: 1
tcgcaagatt aaaactcaaa gga 23

<210> SEQ ID NO 2
<211> LENGTH: 24
<212> TYPE: DNA
<213> ORGANISM: Artificial Sequence
<220> FEATURE:
<223> OTHER INFORMATION: synthetic HLB(1) target capture extender probe HLB 002 CE for Candidatus Liberibacter asiaticus (Huanglongbing (HLB), citrus greening)

<400> SEQUENCE: 2
ggattagata ccctggtagt ccac 24

<210> SEQ ID NO 3
<211> LENGTH: 28
<212> TYPE: DNA
<213> ORGANISM: Artificial Sequence
<220> FEATURE:
<223> OTHER INFORMATION: synthetic HLB(1) target capture extender probe HLB 003 CE for Candidatus Liberibacter asiaticus (Huanglongbing (HLB), citrus greening)

<400> SEQUENCE: 3
agtgtagagg tgaaattcgt agatattc 28

<210> SEQ ID NO 4
<211> LENGTH: 24
<212> TYPE: DNA
<213> ORGANISM: Artificial Sequence
<220> FEATURE:
<223> OTHER INFORMATION: synthetic HLB(1) target capture extender probe HLB 004 CE for Candidatus Liberibacter asiaticus (Huanglongbing (HLB), citrus greening)

<400> SEQUENCE: 4
cggcgattaa gttagaggtg aaat 24

<210> SEQ ID NO 5
<211> LENGTH: 18
<212> TYPE: DNA
<213> ORGANISM: Artificial Sequence
<220> FEATURE:
<223> OTHER INFORMATION: synthetic HLB(1) target capture extender probe HLB 005 CE for Candidatus Liberibacter asiaticus (Huanglongbing (HLB), citrus greening)

<400> SEQUENCE: 5
gcgtaaaggg cgcgtagg 18

<210> SEQ ID NO 6
<211> LENGTH: 21
<212> TYPE: DNA
<213> ORGANISM: Artificial Sequence
<220> FEATURE:
<223> OTHER INFORMATION: synthetic HLB(1) target capture extender probe HLB 006 CE for Candidatus Liberibacter asiaticus (Huanglongbing (HLB), citrus greening)

<400> SEQUENCE: 6
agcgttgttc ggaataactg g 21

<210> SEQ ID NO 7
<211> LENGTH: 18
<212> TYPE: DNA

```
<213> ORGANISM: Artificial Sequence
<220> FEATURE:
<223> OTHER INFORMATION: synthetic HLB(1) target label extender probe
      HLB 007 LE for Candidatus Liberibacter asiaticus (Huanglongbing
      (HLB), citrus greening)

<400> SEQUENCE: 7

tccgcctggg gagtacgg                                                    18


<210> SEQ ID NO 8
<211> LENGTH: 21
<212> TYPE: DNA
<213> ORGANISM: Artificial Sequence
<220> FEATURE:
<223> OTHER INFORMATION: synthetic HLB(1) target label extender probe
      HLB 008 LE for Candidatus Liberibacter asiaticus (Huanglongbing
      (HLB), citrus greening)

<400> SEQUENCE: 8

cgcacgtaac gcattaagca c                                                21


<210> SEQ ID NO 9
<211> LENGTH: 22
<212> TYPE: DNA
<213> ORGANISM: Artificial Sequence
<220> FEATURE:
<223> OTHER INFORMATION: synthetic HLB(1) target label extender probe
      HLB 009 LE for Candidatus Liberibacter asiaticus (Huanglongbing
      (HLB), citrus greening)

<400> SEQUENCE: 9

tgggtggttt accattcagt gg                                               22


<210> SEQ ID NO 10
<211> LENGTH: 25
<212> TYPE: DNA
<213> ORGANISM: Artificial Sequence
<220> FEATURE:
<223> OTHER INFORMATION: synthetic HLB(1) target label extender probe
      HLB 010 LE for Candidatus Liberibacter asiaticus (Huanglongbing
      (HLB), citrus greening)

<400> SEQUENCE: 10

gctgtaaacg atgagtgcta gctgt                                            25


<210> SEQ ID NO 11
<211> LENGTH: 19
<212> TYPE: DNA
<213> ORGANISM: Artificial Sequence
<220> FEATURE:
<223> OTHER INFORMATION: synthetic HLB(1) target label extender probe
      HLB 011 LE for Candidatus Liberibacter asiaticus (Huanglongbing
      (HLB), citrus greening)

<400> SEQUENCE: 11

aaagcgtggg gagcaaaca                                                   19


<210> SEQ ID NO 12
<211> LENGTH: 20
<212> TYPE: DNA
<213> ORGANISM: Artificial Sequence
<220> FEATURE:
<223> OTHER INFORMATION: synthetic HLB(1) target label extender probe
      HLB 012 LE for Candidatus Liberibacter asiaticus (Huanglongbing
      (HLB), citrus greening)

<400> SEQUENCE: 12

gatactgacg ctgaggcgcg                                                  20
```

<210> SEQ ID NO 13
<211> LENGTH: 18
<212> TYPE: DNA
<213> ORGANISM: Artificial Sequence
<220> FEATURE:
<223> OTHER INFORMATION: synthetic HLB(1) target label extender probe
HLB 013 LE for Candidatus Liberibacter asiaticus (Huanglongbing
(HLB), citrus greening)

<400> SEQUENCE: 13
aaggcggctc actggcct 18

<210> SEQ ID NO 14
<211> LENGTH: 18
<212> TYPE: DNA
<213> ORGANISM: Artificial Sequence
<220> FEATURE:
<223> OTHER INFORMATION: synthetic HLB(1) target label extender probe
HLB 014 LE for Candidatus Liberibacter asiaticus (Huanglongbing
(HLB), citrus greening)

<400> SEQUENCE: 14
ggaggaacac cggtggcg 18

<210> SEQ ID NO 15
<211> LENGTH: 21
<212> TYPE: DNA
<213> ORGANISM: Artificial Sequence
<220> FEATURE:
<223> OTHER INFORMATION: synthetic HLB(1) target label extender probe
HLB 015 LE for Candidatus Liberibacter asiaticus (Huanglongbing
(HLB), citrus greening)

<400> SEQUENCE: 15
ggagaggtga gtggaattcc g 21

<210> SEQ ID NO 16
<211> LENGTH: 28
<212> TYPE: DNA
<213> ORGANISM: Artificial Sequence
<220> FEATURE:
<223> OTHER INFORMATION: synthetic HLB(1) target label extender probe
HLB 016 LE for Candidatus Liberibacter asiaticus (Huanglongbing
(HLB), citrus greening)

<400> SEQUENCE: 16
gcctttaata ctgattgtct agagttca 28

<210> SEQ ID NO 17
<211> LENGTH: 17
<212> TYPE: DNA
<213> ORGANISM: Artificial Sequence
<220> FEATURE:
<223> OTHER INFORMATION: synthetic HLB(1) target label extender probe
HLB 017 LE for Candidatus Liberibacter asiaticus (Huanglongbing
(HLB), citrus greening)

<400> SEQUENCE: 17
cttcgtgcca gcagccg 17

<210> SEQ ID NO 18
<211> LENGTH: 19
<212> TYPE: DNA
<213> ORGANISM: Artificial Sequence
<220> FEATURE:
<223> OTHER INFORMATION: synthetic HLB(1) target label extender probe
HLB 018 LE for Candidatus Liberibacter asiaticus (Huanglongbing

```
      (HLB), citrus greening)

<400> SEQUENCE: 18

gagaagaagc cccggctaa                                                  19


<210> SEQ ID NO 19
<211> LENGTH: 21
<212> TYPE: DNA
<213> ORGANISM: Artificial Sequence
<220> FEATURE:
<223> OTHER INFORMATION: synthetic HLB(1) target blocking probe HLB 019
      BL for Candidatus Liberibacter asiaticus (Huanglongbing (HLB),
      citrus greening)

<400> SEQUENCE: 19

cccaggctca accttggaac t                                               21


<210> SEQ ID NO 20
<211> LENGTH: 25
<212> TYPE: DNA
<213> ORGANISM: Artificial Sequence
<220> FEATURE:
<223> OTHER INFORMATION: synthetic HLB(2) target capture extender probe
      HLB 001 CE for Candidatus Liberibacter asiaticus (Huanglongbing
      (HLB), citrus greening)

<400> SEQUENCE: 20

ctcctgtggg ttatagagat tacca                                           25


<210> SEQ ID NO 21
<211> LENGTH: 22
<212> TYPE: DNA
<213> ORGANISM: Artificial Sequence
<220> FEATURE:
<223> OTHER INFORMATION: synthetic HLB(2) target capture extender probe
      HLB 002 CE for Candidatus Liberibacter asiaticus (Huanglongbing
      (HLB), citrus greening)

<400> SEQUENCE: 21

tctcgtcttt acccgaacaa aa                                              22


<210> SEQ ID NO 22
<211> LENGTH: 24
<212> TYPE: DNA
<213> ORGANISM: Artificial Sequence
<220> FEATURE:
<223> OTHER INFORMATION: synthetic HLB(2) target capture extender probe
      HLB 003 CE for Candidatus Liberibacter asiaticus (Huanglongbing
      (HLB), citrus greening)

<400> SEQUENCE: 22

tctccctcac tcaattcaag ttca                                            24


<210> SEQ ID NO 23
<211> LENGTH: 22
<212> TYPE: DNA
<213> ORGANISM: Artificial Sequence
<220> FEATURE:
<223> OTHER INFORMATION: synthetic HLB(2) target capture extender probe
      HLB 004 CE for Candidatus Liberibacter asiaticus (Huanglongbing
      (HLB), citrus greening)

<400> SEQUENCE: 23

cagttgtttt acgctcaccc tc                                              22


<210> SEQ ID NO 24
<211> LENGTH: 23
```

<212> TYPE: DNA
<213> ORGANISM: Artificial Sequence
<220> FEATURE:
<223> OTHER INFORMATION: synthetic HLB(2) target capture extender probe
HLB 005 CE for Candidatus Liberibacter asiaticus (Huanglongbing
(HLB), citrus greening)

<400> SEQUENCE: 24
gctataccta cagaaccagc gct 23

<210> SEQ ID NO 25
<211> LENGTH: 29
<212> TYPE: DNA
<213> ORGANISM: Artificial Sequence
<220> FEATURE:
<223> OTHER INFORMATION: synthetic HLB(2) target label extender probe
HLB 006 LE for Candidatus Liberibacter asiaticus (Huanglongbing
(HLB), citrus greening)

<400> SEQUENCE: 25
tttgaaatct tttcactaga ttctttaat 29

<210> SEQ ID NO 26
<211> LENGTH: 24
<212> TYPE: DNA
<213> ORGANISM: Artificial Sequence
<220> FEATURE:
<223> OTHER INFORMATION: synthetic HLB(2) target label extender probe
HLB 007 LE for Candidatus Liberibacter asiaticus (Huanglongbing
(HLB), citrus greening)

<400> SEQUENCE: 26
ggcctttcac cagaaaagaa atat 24

<210> SEQ ID NO 27
<211> LENGTH: 24
<212> TYPE: DNA
<213> ORGANISM: Artificial Sequence
<220> FEATURE:
<223> OTHER INFORMATION: synthetic HLB(2) target label extender probe
HLB 008 LE for Candidatus Liberibacter asiaticus (Huanglongbing
(HLB), citrus greening)

<400> SEQUENCE: 27
cctctttgca aaatctcgat taat 24

<210> SEQ ID NO 28
<211> LENGTH: 29
<212> TYPE: DNA
<213> ORGANISM: Artificial Sequence
<220> FEATURE:
<223> OTHER INFORMATION: synthetic HLB(2) target label extender probe
HLB 009 LE for Candidatus Liberibacter asiaticus (Huanglongbing
(HLB), citrus greening)

<400> SEQUENCE: 28
tgatcaatca gatactcaat atccactat 29

<210> SEQ ID NO 29
<211> LENGTH: 25
<212> TYPE: DNA
<213> ORGANISM: Artificial Sequence
<220> FEATURE:
<223> OTHER INFORMATION: synthetic HLB(2) target label extender probe
HLB 010 LE for Candidatus Liberibacter asiaticus (Huanglongbing
(HLB), citrus greening)

<400> SEQUENCE: 29
ccgctttaca tataaaggag aacct 25

<210> SEQ ID NO 30
<211> LENGTH: 24
<212> TYPE: DNA
<213> ORGANISM: Artificial Sequence
<220> FEATURE:
<223> OTHER INFORMATION: synthetic HLB(2) target label extender probe
HLB 011 LE for Candidatus Liberibacter asiaticus (Huanglongbing
(HLB), citrus greening)

<400> SEQUENCE: 30
ttgatcattc ccctcaattt ctat 24

<210> SEQ ID NO 31
<211> LENGTH: 26
<212> TYPE: DNA
<213> ORGANISM: Artificial Sequence
<220> FEATURE:
<223> OTHER INFORMATION: synthetic HLB(2) target label extender probe
HLB 012 LE for Candidatus Liberibacter asiaticus (Huanglongbing
(HLB), citrus greening)

<400> SEQUENCE: 31
gctcaatcat ggaataatta attgga 26

<210> SEQ ID NO 32
<211> LENGTH: 22
<212> TYPE: DNA
<213> ORGANISM: Artificial Sequence
<220> FEATURE:
<223> OTHER INFORMATION: synthetic HLB(2) target label extender probe
HLB 013 LE for Candidatus Liberibacter asiaticus (Huanglongbing
(HLB), citrus greening)

<400> SEQUENCE: 32
gccatgatac gacgcttagc ac 22

<210> SEQ ID NO 33
<211> LENGTH: 23
<212> TYPE: DNA
<213> ORGANISM: Artificial Sequence
<220> FEATURE:
<223> OTHER INFORMATION: synthetic HLB(2) target label extender probe
HLB 014 LE for Candidatus Liberibacter asiaticus (Huanglongbing
(HLB), citrus greening)

<400> SEQUENCE: 33
tgacttcaga aaaataaccc gtg 23

<210> SEQ ID NO 34
<211> LENGTH: 20
<212> TYPE: DNA
<213> ORGANISM: Artificial Sequence
<220> FEATURE:
<223> OTHER INFORMATION: synthetic HLB(2) target label extender probe
HLB 015 LE for Candidatus Liberibacter asiaticus (Huanglongbing
(HLB), citrus greening)

<400> SEQUENCE: 34
tgctggcaat tgcgaaatat 20

<210> SEQ ID NO 35
<211> LENGTH: 23
<212> TYPE: DNA
<213> ORGANISM: Artificial Sequence
<220> FEATURE:
<223> OTHER INFORMATION: synthetic HLB(2) target blocker probe HLB 016

BL for Candidatus Liberibacter asiaticus (Huanglongbing (HLB), citrus greening)

<400> SEQUENCE: 35
cgccgaatta cagaatcata cga 23

<210> SEQ ID NO 36
<211> LENGTH: 26
<212> TYPE: DNA
<213> ORGANISM: Artificial Sequence
<220> FEATURE:
<223> OTHER INFORMATION: synthetic HLB(2) target blocker probe HLB 017 BL for Candidatus Liberibacter asiaticus (Huanglongbing (HLB), citrus greening)

<400> SEQUENCE: 36
agaatcacat aatcggatac atcatt 26

<210> SEQ ID NO 37
<211> LENGTH: 21
<212> TYPE: DNA
<213> ORGANISM: Artificial Sequence
<220> FEATURE:
<223> OTHER INFORMATION: synthetic Witches' Broom disease target capture extender probe Witches' Broom 001 CE for Candidatus Phytoplasma aurantifolia

<400> SEQUENCE: 37
cgcattttac cgctacacat g 21

<210> SEQ ID NO 38
<211> LENGTH: 23
<212> TYPE: DNA
<213> ORGANISM: Artificial Sequence
<220> FEATURE:
<223> OTHER INFORMATION: synthetic Witches' Broom disease target capture extender probe Witches' Broom 002 CE for Candidatus Phytoplasma aurantifolia

<400> SEQUENCE: 38
tcgggtatct tcgaattaaa caa 23

<210> SEQ ID NO 39
<211> LENGTH: 24
<212> TYPE: DNA
<213> ORGANISM: Artificial Sequence
<220> FEATURE:
<223> OTHER INFORMATION: synthetic Witches' Broom disease target capture extender probe Witches' Broom 003 CE for Candidatus Phytoplasma aurantifolia

<400> SEQUENCE: 39
catgtcaaga cctggtaagg tttt 24

<210> SEQ ID NO 40
<211> LENGTH: 21
<212> TYPE: DNA
<213> ORGANISM: Artificial Sequence
<220> FEATURE:
<223> OTHER INFORMATION: synthetic Witches' Broom disease target capture extender probe Witches' Broom 004 CE for Candidatus Phytoplasma aurantifolia

<400> SEQUENCE: 40
gcagtctcgt taaagtcccc a 21

<210> SEQ ID NO 41

-continued

<211> LENGTH: 22
<212> TYPE: DNA
<213> ORGANISM: Artificial Sequence
<220> FEATURE:
<223> OTHER INFORMATION: synthetic Witches' Broom disease target capture extender probe Witches' Broom 005 CE for Candidatus Phytoplasma aurantifolia

<400> SEQUENCE: 41
gcatgatgat ttgacgtgat cc 22

<210> SEQ ID NO 42
<211> LENGTH: 21
<212> TYPE: DNA
<213> ORGANISM: Artificial Sequence
<220> FEATURE:
<223> OTHER INFORMATION: synthetic Witches' Broom disease target capture extender probe Witches' Broom 006 CE for Candidatus Phytoplasma aurantifolia

<400> SEQUENCE: 42
ttgtagccca ggtcataagg g 21

<210> SEQ ID NO 43
<211> LENGTH: 25
<212> TYPE: DNA
<213> ORGANISM: Artificial Sequence
<220> FEATURE:
<223> OTHER INFORMATION: synthetic Witches' Broom disease target label extender probe Witches' Broom 007 LE for Candidatus Phytoplasma aurantifolia

<400> SEQUENCE: 43
cctctggtgt tcctccatat attta 25

<210> SEQ ID NO 44
<211> LENGTH: 17
<212> TYPE: DNA
<213> ORGANISM: Artificial Sequence
<220> FEATURE:
<223> OTHER INFORMATION: synthetic Witches' Broom disease target label extender probe Witches' Broom 008 LE for Candidatus Phytoplasma aurantifolia

<400> SEQUENCE: 44
ccagcaagcc gcctacg 17

<210> SEQ ID NO 45
<211> LENGTH: 22
<212> TYPE: DNA
<213> ORGANISM: Artificial Sequence
<220> FEATURE:
<223> OTHER INFORMATION: synthetic Witches' Broom disease target label extender probe Witches' Broom 009 LE for Candidatus Phytoplasma aurantifolia

<400> SEQUENCE: 45
gtgcctcagc gtcagtaaag ac 22

<210> SEQ ID NO 46
<211> LENGTH: 19
<212> TYPE: DNA
<213> ORGANISM: Artificial Sequence
<220> FEATURE:
<223> OTHER INFORMATION: synthetic Witches' Broom disease target label extender probe Witches' Broom 010 LE for Candidatus Phytoplasma aurantifolia

<400> SEQUENCE: 46
gtttgctccc cacgctttc 19

<210> SEQ ID NO 47
<211> LENGTH: 24
<212> TYPE: DNA
<213> ORGANISM: Artificial Sequence
<220> FEATURE:
<223> OTHER INFORMATION: synthetic Witches' Broom disease target label extender probe Witches' Broom 011 LE for Candidatus Phytoplasma aurantifolia

<400> SEQUENCE: 47
tggactacca gggtatctaa tcct 24

<210> SEQ ID NO 48
<211> LENGTH: 23
<212> TYPE: DNA
<213> ORGANISM: Artificial Sequence
<220> FEATURE:
<223> OTHER INFORMATION: synthetic Witches' Broom disease target label extender probe Witches' Broom 012 LE for Candidatus Phytoplasma aurantifolia

<400> SEQUENCE: 48
cttagtactc atcgtttacg gcg 23

<210> SEQ ID NO 49
<211> LENGTH: 21
<212> TYPE: DNA
<213> ORGANISM: Artificial Sequence
<220> FEATURE:
<223> OTHER INFORMATION: synthetic Witches' Broom disease target label extender probe Witches' Broom 013 LE for Candidatus Phytoplasma aurantifolia

<400> SEQUENCE: 49
cagtaccggt ttaacccgac a 21

<210> SEQ ID NO 50
<211> LENGTH: 25
<212> TYPE: DNA
<213> ORGANISM: Artificial Sequence
<220> FEATURE:
<223> OTHER INFORMATION: synthetic Witches' Broom disease target label extender probe Witches' Broom 014 LE for Candidatus Phytoplasma aurantifolia

<400> SEQUENCE: 50
ggcggagtac ttaatgtgtt aactt 25

<210> SEQ ID NO 51
<211> LENGTH: 26
<212> TYPE: DNA
<213> ORGANISM: Artificial Sequence
<220> FEATURE:
<223> OTHER INFORMATION: synthetic Witches' Broom disease target label extender probe Witches' Broom 015 LE for Candidatus Phytoplasma aurantifolia

<400> SEQUENCE: 51
tttcatactt gcgtacgtac tactca 26

<210> SEQ ID NO 52
<211> LENGTH: 23
<212> TYPE: DNA
<213> ORGANISM: Artificial Sequence
<220> FEATURE:

<223> OTHER INFORMATION: synthetic Witches' Broom disease target label extender probe Witches' Broom 016 LE for Candidatus Phytoplasma aurantifolia

<400> SEQUENCE: 52
ggagtcccgt caattccttt aag 23

<210> SEQ ID NO 53
<211> LENGTH: 28
<212> TYPE: DNA
<213> ORGANISM: Artificial Sequence
<220> FEATURE:
<223> OTHER INFORMATION: synthetic Witches' Broom disease target label extender probe Witches' Broom 017 LE for Candidatus Phytoplasma aurantifolia

<400> SEQUENCE: 53
ccactatatt actatagctt cgcaaaaa 28

<210> SEQ ID NO 54
<211> LENGTH: 24
<212> TYPE: DNA
<213> ORGANISM: Artificial Sequence
<220> FEATURE:
<223> OTHER INFORMATION: synthetic Witches' Broom disease target label extender probe Witches' Broom 018 LE for Candidatus Phytoplasma aurantifolia

<400> SEQUENCE: 54
caccacctgt gtttctgata acct 24

<210> SEQ ID NO 55
<211> LENGTH: 19
<212> TYPE: DNA
<213> ORGANISM: Artificial Sequence
<220> FEATURE:
<223> OTHER INFORMATION: synthetic Witches' Broom disease target blocking probe Witches' Broom 019 BL for Candidatus Phytoplasma aurantifolia

<400> SEQUENCE: 55
catgatccac cgcttgtgc 19

<210> SEQ ID NO 56
<211> LENGTH: 20
<212> TYPE: DNA
<213> ORGANISM: Artificial Sequence
<220> FEATURE:
<223> OTHER INFORMATION: synthetic Witches' Broom disease target blocking probe Witches' Broom 020 BL for Candidatus Phytoplasma aurantifolia

<400> SEQUENCE: 56
acgagctgac gacaaccatg 20

<210> SEQ ID NO 57
<211> LENGTH: 26
<212> TYPE: DNA
<213> ORGANISM: Artificial Sequence
<220> FEATURE:
<223> OTHER INFORMATION: synthetic Witches' Broom disease target blocking probe Witches' Broom 021 BL for Candidatus Phytoplasma aurantifolia

<400> SEQUENCE: 57
ttaggactta acctaacatc tcacga 26

<210> SEQ ID NO 58
<211> LENGTH: 19
<212> TYPE: DNA
<213> ORGANISM: Artificial Sequence
<220> FEATURE:
<223> OTHER INFORMATION: synthetic Witches' Broom disease target blocking probe Witches' Broom 022 BL for Candidatus Phytoplasma aurantifolia

<400> SEQUENCE: 58
gataagggtt gcgctcgtt 19

<210> SEQ ID NO 59
<211> LENGTH: 21
<212> TYPE: DNA
<213> ORGANISM: Artificial Sequence
<220> FEATURE:
<223> OTHER INFORMATION: synthetic Witches' Broom disease target blocking probe Witches' Broom 023 BL for Candidatus Phytoplasma aurantifolia

<400> SEQUENCE: 59
ccataacgtg ctggcaacta a 21

<210> SEQ ID NO 60
<211> LENGTH: 24
<212> TYPE: DNA
<213> ORGANISM: Artificial Sequence
<220> FEATURE:
<223> OTHER INFORMATION: synthetic Witches' Broom disease target blocking probe Witches' Broom 024 BL for Candidatus Phytoplasma aurantifolia

<400> SEQUENCE: 60
tcaccttcct ccaatttatc attg 24

<210> SEQ ID NO 61
<211> LENGTH: 19
<212> TYPE: DNA
<213> ORGANISM: Artificial Sequence
<220> FEATURE:
<223> OTHER INFORMATION: synthetic citrus canker target capture extender probe Canker 001 CE for Xanthomonas axonopodis pv citri

<400> SEQUENCE: 61
gctgaccatg ccgcatgtg 19

<210> SEQ ID NO 62
<211> LENGTH: 20
<212> TYPE: DNA
<213> ORGANISM: Artificial Sequence
<220> FEATURE:
<223> OTHER INFORMATION: synthetic citrus canker target capture extender probe Canker 002 CE for Xanthomonas axonopodis pv citri

<400> SEQUENCE: 62
cggcgacttc gactatctgc 20

<210> SEQ ID NO 63
<211> LENGTH: 20
<212> TYPE: DNA
<213> ORGANISM: Artificial Sequence
<220> FEATURE:
<223> OTHER INFORMATION: synthetic citrus canker target capture extender probe Canker 003 CE for Xanthomonas axonopodis pv citri

<400> SEQUENCE: 63
ctggagtgcc acctggtctc 20

<210> SEQ ID NO 64
<211> LENGTH: 19
<212> TYPE: DNA
<213> ORGANISM: Artificial Sequence
<220> FEATURE:
<223> OTHER INFORMATION: synthetic citrus canker target capture extender
probe Canker 004 CE for Xanthomonas axonopodis pv citri

<400> SEQUENCE: 64
ccggcgatat cttcgaaga 19

<210> SEQ ID NO 65
<211> LENGTH: 19
<212> TYPE: DNA
<213> ORGANISM: Artificial Sequence
<220> FEATURE:
<223> OTHER INFORMATION: synthetic citrus canker target capture extender
probe Canker 005 CE for Xanthomonas axonopodis pv citri

<400> SEQUENCE: 65
ccgcactacc tcaaggcca 19

<210> SEQ ID NO 66
<211> LENGTH: 16
<212> TYPE: DNA
<213> ORGANISM: Artificial Sequence
<220> FEATURE:
<223> OTHER INFORMATION: synthetic citrus canker target capture extender
probe Canker 006 CE for Xanthomonas axonopodis pv citri

<400> SEQUENCE: 66
ggcgccatca ccggct 16

<210> SEQ ID NO 67
<211> LENGTH: 17
<212> TYPE: DNA
<213> ORGANISM: Artificial Sequence
<220> FEATURE:
<223> OTHER INFORMATION: synthetic citrus canker target capture extender
probe Canker 007 CE for Xanthomonas axonopodis pv citri

<400> SEQUENCE: 67
cctgtcgacc acgccgt 17

<210> SEQ ID NO 68
<211> LENGTH: 21
<212> TYPE: DNA
<213> ORGANISM: Artificial Sequence
<220> FEATURE:
<223> OTHER INFORMATION: synthetic citrus canker target label extender
probe Canker 008 LE for Xanthomonas axonopodis pv citri

<400> SEQUENCE: 68
tggaagaggt caaggagacg c 21

<210> SEQ ID NO 69
<211> LENGTH: 25
<212> TYPE: DNA
<213> ORGANISM: Artificial Sequence
<220> FEATURE:
<223> OTHER INFORMATION: synthetic citrus canker target label extender
probe Canker 009 LE for Xanthomonas axonopodis pv citri

<400> SEQUENCE: 69
cgtgaatcca agagctatat cgtga 25

```
<210> SEQ ID NO 70
<211> LENGTH: 19
<212> TYPE: DNA
<213> ORGANISM: Artificial Sequence
<220> FEATURE:
<223> OTHER INFORMATION: synthetic citrus canker target label extender
      probe Canker 010 LE for Xanthomonas axonopodis pv citri

<400> SEQUENCE: 70

gagatggcgt cctaccgca                                                 19


<210> SEQ ID NO 71
<211> LENGTH: 17
<212> TYPE: DNA
<213> ORGANISM: Artificial Sequence
<220> FEATURE:
<223> OTHER INFORMATION: synthetic citrus canker target label extender
      probe Canker 011 LE for Xanthomonas axonopodis pv citri

<400> SEQUENCE: 71

tcaaggcgcg catcagc                                                   17


<210> SEQ ID NO 72
<211> LENGTH: 19
<212> TYPE: DNA
<213> ORGANISM: Artificial Sequence
<220> FEATURE:
<223> OTHER INFORMATION: synthetic citrus canker target label extender
      probe Canker 012 LE for Xanthomonas axonopodis pv citri

<400> SEQUENCE: 72

gctaaagctg cccaacgtg                                                 19


<210> SEQ ID NO 73
<211> LENGTH: 15
<212> TYPE: DNA
<213> ORGANISM: Artificial Sequence
<220> FEATURE:
<223> OTHER INFORMATION: synthetic citrus canker target label extender
      probe Canker 013 LE for Xanthomonas axonopodis pv citri

<400> SEQUENCE: 73

attccgccgc gccgc                                                     15


<210> SEQ ID NO 74
<211> LENGTH: 21
<212> TYPE: DNA
<213> ORGANISM: Artificial Sequence
<220> FEATURE:
<223> OTHER INFORMATION: synthetic citrus canker target label extender
      probe Canker 014 LE for Xanthomonas axonopodis pv citri

<400> SEQUENCE: 74

agatcagcct ggcctacaaa t                                              21


<210> SEQ ID NO 75
<211> LENGTH: 18
<212> TYPE: DNA
<213> ORGANISM: Artificial Sequence
<220> FEATURE:
<223> OTHER INFORMATION: synthetic citrus canker target label extender
      probe Canker 015 LE for Xanthomonas axonopodis pv citri

<400> SEQUENCE: 75

gcctgctggt gttcgtgg                                                  18
```

<210> SEQ ID NO 76
<211> LENGTH: 16
<212> TYPE: DNA
<213> ORGANISM: Artificial Sequence
<220> FEATURE:
<223> OTHER INFORMATION: synthetic citrus canker target label extender
probe Canker 016 LE for Xanthomonas axonopodis pv citri

<400> SEQUENCE: 76
acggctggag cgcgac 16

<210> SEQ ID NO 77
<211> LENGTH: 16
<212> TYPE: DNA
<213> ORGANISM: Artificial Sequence
<220> FEATURE:
<223> OTHER INFORMATION: synthetic citrus canker target label extender
probe Canker 017 LE for Xanthomonas axonopodis pv citri

<400> SEQUENCE: 77
gcaccgagcg cgtgcg 16

<210> SEQ ID NO 78
<211> LENGTH: 16
<212> TYPE: DNA
<213> ORGANISM: Artificial Sequence
<220> FEATURE:
<223> OTHER INFORMATION: synthetic citrus canker target label extender
probe Canker 018 LE for Xanthomonas axonopodis pv citri

<400> SEQUENCE: 78
tgggcgagcg ggtcgg 16

<210> SEQ ID NO 79
<211> LENGTH: 21
<212> TYPE: DNA
<213> ORGANISM: Artificial Sequence
<220> FEATURE:
<223> OTHER INFORMATION: synthetic citrus canker target label extender
probe Canker 019 LE for Xanthomonas axonopodis pv citri

<400> SEQUENCE: 79
ggcggatttc gtttaccgaa c 21

<210> SEQ ID NO 80
<211> LENGTH: 19
<212> TYPE: DNA
<213> ORGANISM: Artificial Sequence
<220> FEATURE:
<223> OTHER INFORMATION: synthetic citrus canker target label extender
probe Canker 020 LE for Xanthomonas axonopodis pv citri

<400> SEQUENCE: 80
cgcatcctgc agcaggagg 19

<210> SEQ ID NO 81
<211> LENGTH: 20
<212> TYPE: DNA
<213> ORGANISM: Artificial Sequence
<220> FEATURE:
<223> OTHER INFORMATION: synthetic citrus canker target label extender
probe Canker 021 LE for Xanthomonas axonopodis pv citri

<400> SEQUENCE: 81
agatcgaccg caagatcctg 20

<210> SEQ ID NO 82

<211> LENGTH: 19
<212> TYPE: DNA
<213> ORGANISM: Artificial Sequence
<220> FEATURE:
<223> OTHER INFORMATION: synthetic citrus canker target blocking probe
Canker 022 BL for Xanthomonas axonopodis pv citri

<400> SEQUENCE: 82
agttgctcgg cagcacctt 19

<210> SEQ ID NO 83
<211> LENGTH: 17
<212> TYPE: DNA
<213> ORGANISM: Artificial Sequence
<220> FEATURE:
<223> OTHER INFORMATION: synthetic citrus canker target blocking probe
Canker 023 BL for Xanthomonas axonopodis pv citri

<400> SEQUENCE: 83
cttacgcgcg gctggac 17

<210> SEQ ID NO 84
<211> LENGTH: 22
<212> TYPE: DNA
<213> ORGANISM: Artificial Sequence
<220> FEATURE:
<223> OTHER INFORMATION: synthetic citrus variegated chlorosis CVC(1)
target capture extender probe CVC 001 CE for
Xylella fastidiosa subspecies pauca

<400> SEQUENCE: 84
caatccctga tgtttgtgca ga 22

<210> SEQ ID NO 85
<211> LENGTH: 25
<212> TYPE: DNA
<213> ORGANISM: Artificial Sequence
<220> FEATURE:
<223> OTHER INFORMATION: synthetic citrus variegated chlorosis CVC(1)
target capture extender probe CVC 002 CE for
Xylella fastidiosa subspecies pauca

<400> SEQUENCE: 85
gtttgcaatc tgtatctgtt tctga 25

<210> SEQ ID NO 86
<211> LENGTH: 22
<212> TYPE: DNA
<213> ORGANISM: Artificial Sequence
<220> FEATURE:
<223> OTHER INFORMATION: synthetic citrus variegated chlorosis CVC(1)
target capture extender probe CVC 003 CE for
Xylella fastidiosa subspecies pauca

<400> SEQUENCE: 86
gcttcaaacg ctgcaaagtt tc 22

<210> SEQ ID NO 87
<211> LENGTH: 23
<212> TYPE: DNA
<213> ORGANISM: Artificial Sequence
<220> FEATURE:
<223> OTHER INFORMATION: synthetic citrus variegated chlorosis CVC(1)
target capture extender probe CVC 004 CE for
Xylella fastidiosa subspecies pauca

<400> SEQUENCE: 87
tccagtacag tggattcctg ttg 23

<210> SEQ ID NO 88
<211> LENGTH: 22
<212> TYPE: DNA
<213> ORGANISM: Artificial Sequence
<220> FEATURE:
<223> OTHER INFORMATION: synthetic citrus variegated chlorosis CVC(1)
      target capture extender probe CVC 005 CE for
      Xylella fastidiosa subspecies pauca

<400> SEQUENCE: 88
ttcccttaag gattgttgca ac 22

<210> SEQ ID NO 89
<211> LENGTH: 24
<212> TYPE: DNA
<213> ORGANISM: Artificial Sequence
<220> FEATURE:
<223> OTHER INFORMATION: synthetic citrus variegated chlorosis CVC(1)
      target capture extender probe CVC 006 CE for
      Xylella fastidiosa subspecies pauca

<400> SEQUENCE: 89
ctgagacttg acaatctggg tagc 24

<210> SEQ ID NO 90
<211> LENGTH: 20
<212> TYPE: DNA
<213> ORGANISM: Artificial Sequence
<220> FEATURE:
<223> OTHER INFORMATION: synthetic citrus variegated chlorosis CVC(1)
      target label extender probe CVC 007 LE for
      Xylella fastidiosa subspecies pauca

<400> SEQUENCE: 90
gttgacccat cgacaatccc 20

<210> SEQ ID NO 91
<211> LENGTH: 20
<212> TYPE: DNA
<213> ORGANISM: Artificial Sequence
<220> FEATURE:
<223> OTHER INFORMATION: synthetic citrus variegated chlorosis CVC(1)
      target label extender probe CVC 008 LE for
      Xylella fastidiosa subspecies pauca

<400> SEQUENCE: 91
tagcacttgc gcttgagctt 20

<210> SEQ ID NO 92
<211> LENGTH: 20
<212> TYPE: DNA
<213> ORGANISM: Artificial Sequence
<220> FEATURE:
<223> OTHER INFORMATION: synthetic citrus variegated chlorosis CVC(1)
      target label extender probe CVC 009 LE for
      Xylella fastidiosa subspecies pauca

<400> SEQUENCE: 92
tttgtgccaa ttcacgttgc 20

<210> SEQ ID NO 93
<211> LENGTH: 22
<212> TYPE: DNA
<213> ORGANISM: Artificial Sequence
<220> FEATURE:
<223> OTHER INFORMATION: synthetic citrus variegated chlorosis CVC(1)
      target label extender probe CVC 010 LE for -continued Xylella fastidiosa subspecies pauca

<400> SEQUENCE: 93
acataacgcg catcctctaa ct 22

<210> SEQ ID NO 94
<211> LENGTH: 19
<212> TYPE: DNA
<213> ORGANISM: Artificial Sequence
<220> FEATURE:
<223> OTHER INFORMATION: synthetic citrus variegated chlorosis CVC(1)
target label extender probe CVC 011 LE for
Xylella fastidiosa subspecies pauca

<400> SEQUENCE: 94
tttgatttgg agggtgccc 19

<210> SEQ ID NO 95
<211> LENGTH: 20
<212> TYPE: DNA
<213> ORGANISM: Artificial Sequence
<220> FEATURE:
<223> OTHER INFORMATION: synthetic citrus variegated chlorosis CVC(1)
target label extender probe CVC 012 LE for
Xylella fastidiosa subspecies pauca

<400> SEQUENCE: 95
cctgcatctg gctcgtgtaa 20

<210> SEQ ID NO 96
<211> LENGTH: 23
<212> TYPE: DNA
<213> ORGANISM: Artificial Sequence
<220> FEATURE:
<223> OTHER INFORMATION: synthetic citrus variegated chlorosis CVC(1)
target label extender probe CVC 013 LE for
Xylella fastidiosa subspecies pauca

<400> SEQUENCE: 96
catgatagct tgacgttgca ttg 23

<210> SEQ ID NO 97
<211> LENGTH: 19
<212> TYPE: DNA
<213> ORGANISM: Artificial Sequence
<220> FEATURE:
<223> OTHER INFORMATION: synthetic citrus variegated chlorosis CVC(1)
target label extender probe CVC 014 LE for
Xylella fastidiosa subspecies pauca

<400> SEQUENCE: 97
aaacaaccga aagcgcacc 19

<210> SEQ ID NO 98
<211> LENGTH: 20
<212> TYPE: DNA
<213> ORGANISM: Artificial Sequence
<220> FEATURE:
<223> OTHER INFORMATION: synthetic citrus variegated chlorosis CVC(1)
target label extender probe CVC 015 LE for
Xylella fastidiosa subspecies pauca

<400> SEQUENCE: 98
cacgattcca tcaattgggg 20

<210> SEQ ID NO 99
<211> LENGTH: 22

<212> TYPE: DNA
<213> ORGANISM: Artificial Sequence
<220> FEATURE:
<223> OTHER INFORMATION: synthetic citrus variegated chlorosis CVC(1) target blocking probe CVC 016 BL for Xylella fastidiosa subspecies pauca

<400> SEQUENCE: 99
cgagtcgcaa tctcaatttc ga 22

<210> SEQ ID NO 100
<211> LENGTH: 20
<212> TYPE: DNA
<213> ORGANISM: Artificial Sequence
<220> FEATURE:
<223> OTHER INFORMATION: synthetic citrus variegated chlorosis CVC(1) target blocking probe CVC 017 BL for Xylella fastidiosa subspecies pauca

<400> SEQUENCE: 100
tgagcaatag accgtcgcgt 20

<210> SEQ ID NO 101
<211> LENGTH: 18
<212> TYPE: DNA
<213> ORGANISM: Artificial Sequence
<220> FEATURE:
<223> OTHER INFORMATION: synthetic citrus variegated chlorosis CVC(1) target blocking probe CVC 018 BL for Xylella fastidiosa subspecies pauca

<400> SEQUENCE: 101
cctgctccag ttgcgcca 18

<210> SEQ ID NO 102
<211> LENGTH: 23
<212> TYPE: DNA
<213> ORGANISM: Artificial Sequence
<220> FEATURE:
<223> OTHER INFORMATION: synthetic citrus variegated chlorosis CVC(1) target blocking probe CVC 019 BL for Xylella fastidiosa subspecies pauca

<400> SEQUENCE: 102
acgagcctca gtttctacct ttt 23

<210> SEQ ID NO 103
<211> LENGTH: 22
<212> TYPE: DNA
<213> ORGANISM: Artificial Sequence
<220> FEATURE:
<223> OTHER INFORMATION: synthetic citrus variegated chlorosis CVC(2) target capture extender probe CVC 001 CE for Xylella fastidiosa subspecies pauca

<400> SEQUENCE: 103
tgcatccact acaggcaatt tt 22

<210> SEQ ID NO 104
<211> LENGTH: 21
<212> TYPE: DNA
<213> ORGANISM: Artificial Sequence
<220> FEATURE:
<223> OTHER INFORMATION: synthetic citrus variegated chlorosis CVC(2) target capture extender probe CVC 002 CE for Xylella fastidiosa subspecies pauca

<400> SEQUENCE: 104

-continued cgattgcgat tggtactacg g 21

<210> SEQ ID NO 105
<211> LENGTH: 21
<212> TYPE: DNA
<213> ORGANISM: Artificial Sequence
<220> FEATURE:
<223> OTHER INFORMATION: synthetic citrus variegated chlorosis CVC(2)
target capture extender probe CVC 003 CE for
Xylella fastidiosa subspecies pauca

<400> SEQUENCE: 105
ggttccaaaa cggatgggaa t 21

<210> SEQ ID NO 106
<211> LENGTH: 21
<212> TYPE: DNA
<213> ORGANISM: Artificial Sequence
<220> FEATURE:
<223> OTHER INFORMATION: synthetic citrus variegated chlorosis CVC(2)
target capture extender probe CVC 004 CE for
Xylella fastidiosa subspecies pauca

<400> SEQUENCE: 106
gcattgctac catgaatggc t 21

<210> SEQ ID NO 107
<211> LENGTH: 22
<212> TYPE: DNA
<213> ORGANISM: Artificial Sequence
<220> FEATURE:
<223> OTHER INFORMATION: synthetic citrus variegated chlorosis CVC(2)
target capture extender probe CVC 005 CE for
Xylella fastidiosa subspecies pauca

<400> SEQUENCE: 107
acttattcta tgcgcctagg ca 22

<210> SEQ ID NO 108
<211> LENGTH: 21
<212> TYPE: DNA
<213> ORGANISM: Artificial Sequence
<220> FEATURE:
<223> OTHER INFORMATION: synthetic citrus variegated chlorosis CVC(2)
target capture extender probe CVC 006 CE for
Xylella fastidiosa subspecies pauca

<400> SEQUENCE: 108
aaacctggtt cttggtgggt c 21

<210> SEQ ID NO 109
<211> LENGTH: 22
<212> TYPE: DNA
<213> ORGANISM: Artificial Sequence
<220> FEATURE:
<223> OTHER INFORMATION: synthetic citrus variegated chlorosis CVC(2)
target label extender probe CVC 007 LE for
Xylella fastidiosa subspecies pauca

<400> SEQUENCE: 109
cattgacatc aattgccaat gg 22

<210> SEQ ID NO 110
<211> LENGTH: 22
<212> TYPE: DNA
<213> ORGANISM: Artificial Sequence
<220> FEATURE:
<223> OTHER INFORMATION: synthetic citrus variegated chlorosis CVC(2)

target label extender probe CVC 008 LE for
Xylella fastidiosa subspecies pauca

<400> SEQUENCE: 110
gcgatagcga taggtaatgg ag 22

<210> SEQ ID NO 111
<211> LENGTH: 18
<212> TYPE: DNA
<213> ORGANISM: Artificial Sequence
<220> FEATURE:
<223> OTHER INFORMATION: synthetic citrus variegated chlorosis CVC(2)
target label extender probe CVC 009 LE for
Xylella fastidiosa subspecies pauca

<400> SEQUENCE: 111
gccatcggtt cagggcaa 18

<210> SEQ ID NO 112
<211> LENGTH: 20
<212> TYPE: DNA
<213> ORGANISM: Artificial Sequence
<220> FEATURE:
<223> OTHER INFORMATION: synthetic citrus variegated chlorosis CVC(2)
target label extender probe CVC 010 LE for
Xylella fastidiosa subspecies pauca

<400> SEQUENCE: 112
cggctggcat agattcgatt 20

<210> SEQ ID NO 113
<211> LENGTH: 23
<212> TYPE: DNA
<213> ORGANISM: Artificial Sequence
<220> FEATURE:
<223> OTHER INFORMATION: synthetic citrus variegated chlorosis CVC(2)
target label extender probe CVC 011 LE for
Xylella fastidiosa subspecies pauca

<400> SEQUENCE: 113
ggctagtcga tatttctggt gca 23

<210> SEQ ID NO 114
<211> LENGTH: 26
<212> TYPE: DNA
<213> ORGANISM: Artificial Sequence
<220> FEATURE:
<223> OTHER INFORMATION: synthetic citrus variegated chlorosis CVC(2)
target label extender probe CVC 012 LE for
Xylella fastidiosa subspecies pauca

<400> SEQUENCE: 114
cttatatgtc aatgagggta aactcg 26

<210> SEQ ID NO 115
<211> LENGTH: 28
<212> TYPE: DNA
<213> ORGANISM: Artificial Sequence
<220> FEATURE:
<223> OTHER INFORMATION: synthetic citrus variegated chlorosis CVC(2)
target label extender probe CVC 013 LE for
Xylella fastidiosa subspecies pauca

<400> SEQUENCE: 115
cagagtattc cctgttttat gattatag 28

<210> SEQ ID NO 116

<211> LENGTH: 20
<212> TYPE: DNA
<213> ORGANISM: Artificial Sequence
<220> FEATURE:
<223> OTHER INFORMATION: synthetic citrus variegated chlorosis CVC(2)
target label extender probe CVC 014 LE for
Xylella fastidiosa subspecies pauca

<400> SEQUENCE: 116
caagccagat ttcacgcaaa 20

<210> SEQ ID NO 117
<211> LENGTH: 27
<212> TYPE: DNA
<213> ORGANISM: Artificial Sequence
<220> FEATURE:
<223> OTHER INFORMATION: synthetic citrus variegated chlorosis CVC(2)
target label extender probe CVC 015 LE for
Xylella fastidiosa subspecies pauca

<400> SEQUENCE: 117
cattcatagt gcttctaacg ataaatg 27

<210> SEQ ID NO 118
<211> LENGTH: 26
<212> TYPE: DNA
<213> ORGANISM: Artificial Sequence
<220> FEATURE:
<223> OTHER INFORMATION: synthetic citrus variegated chlorosis CVC(2)
target label extender probe CVC 016 LE for
Xylella fastidiosa subspecies pauca

<400> SEQUENCE: 118
gctcaagtct atgtaaattc cgactc 26

<210> SEQ ID NO 119
<211> LENGTH: 23
<212> TYPE: DNA
<213> ORGANISM: Artificial Sequence
<220> FEATURE:
<223> OTHER INFORMATION: synthetic citrus variegated chlorosis CVC(2)
target label extender probe CVC 017 LE for
Xylella fastidiosa subspecies pauca

<400> SEQUENCE: 119
ggcgacagta gtcagacatc ctt 23

<210> SEQ ID NO 120
<211> LENGTH: 25
<212> TYPE: DNA
<213> ORGANISM: Artificial Sequence
<220> FEATURE:
<223> OTHER INFORMATION: synthetic citrus variegated chlorosis CVC(2)
target label extender probe CVC 018 LE for
Xylella fastidiosa subspecies pauca

<400> SEQUENCE: 120
gactgaaaat tgcgtagaaa tactg 25

<210> SEQ ID NO 121
<211> LENGTH: 20
<212> TYPE: DNA
<213> ORGANISM: Artificial Sequence
<220> FEATURE:
<223> OTHER INFORMATION: synthetic citrus variegated chlorosis CVC(2)
target label extender probe CVC 019 LE for
Xylella fastidiosa subspecies pauca

<400> SEQUENCE: 121
gcgatttcta tagggaccgg 20

<210> SEQ ID NO 122
<211> LENGTH: 20
<212> TYPE: DNA
<213> ORGANISM: Artificial Sequence
<220> FEATURE:
<223> OTHER INFORMATION: synthetic citrus variegated chlorosis CVC(2) target label extender probe CVC 020 LE for Xylella fastidiosa subspecies pauca

<400> SEQUENCE: 122
cccgttcgca atctcaagat 20

<210> SEQ ID NO 123
<211> LENGTH: 18
<212> TYPE: DNA
<213> ORGANISM: Artificial Sequence
<220> FEATURE:
<223> OTHER INFORMATION: synthetic citrus variegated chlorosis CVC(2) target label extender probe CVC 021 LE for Xylella fastidiosa subspecies pauca

<400> SEQUENCE: 123
tagcacaggg gctgcgtt 18

<210> SEQ ID NO 124
<211> LENGTH: 16
<212> TYPE: DNA
<213> ORGANISM: Artificial Sequence
<220> FEATURE:
<223> OTHER INFORMATION: synthetic citrus variegated chlorosis CVC(2) target blocking probe CVC 022 BL for Xylella fastidiosa subspecies pauca

<400> SEQUENCE: 124
accagcggcg ccactg 16

<210> SEQ ID NO 125
<211> LENGTH: 27
<212> TYPE: DNA
<213> ORGANISM: Artificial Sequence
<220> FEATURE:
<223> OTHER INFORMATION: synthetic citrus stubborn disease target capture extender probe Stubborn 001 CE for Spiroplasma citri

<400> SEQUENCE: 125
ttgtctgaca attcaacaac atattta 27

<210> SEQ ID NO 126
<211> LENGTH: 27
<212> TYPE: DNA
<213> ORGANISM: Artificial Sequence
<220> FEATURE:
<223> OTHER INFORMATION: synthetic citrus stubborn disease target capture extender probe Stubborn 002 CE for Spiroplasma citri

<400> SEQUENCE: 126
aaataaacat tgttggtatg acctaag 27

<210> SEQ ID NO 127
<211> LENGTH: 26
<212> TYPE: DNA
<213> ORGANISM: Artificial Sequence
<220> FEATURE:
<223> OTHER INFORMATION: synthetic citrus stubborn disease target capture extender probe Stubborn 003 CE for Spiroplasma citri

<400> SEQUENCE: 127 cttttcttt cttttcgttt atttgt 26

<210> SEQ ID NO 128
<211> LENGTH: 24
<212> TYPE: DNA
<213> ORGANISM: Artificial Sequence
<220> FEATURE:
<223> OTHER INFORMATION: synthetic citrus stubborn disease target capture extender probe Stubborn 004 CE for Spiroplasma citri

<400> SEQUENCE: 128
ttcgctcata tttcaaactg tttg 24

<210> SEQ ID NO 129
<211> LENGTH: 26
<212> TYPE: DNA
<213> ORGANISM: Artificial Sequence
<220> FEATURE:
<223> OTHER INFORMATION: synthetic citrus stubborn disease target capture extender probe Stubborn 005 CE for Spiroplasma citri

<400> SEQUENCE: 129
aagttgacta tcacttgcta gttgct 26

<210> SEQ ID NO 130
<211> LENGTH: 22
<212> TYPE: DNA
<213> ORGANISM: Artificial Sequence
<220> FEATURE:
<223> OTHER INFORMATION: synthetic citrus stubborn disease target capture extender probe Stubborn 006 CE for Spiroplasma citri

<400> SEQUENCE: 130
ctgtctttga tttgcaaggt aa 22

<210> SEQ ID NO 131
<211> LENGTH: 23
<212> TYPE: DNA
<213> ORGANISM: Artificial Sequence
<220> FEATURE:
<223> OTHER INFORMATION: synthetic citrus stubborn disease target label extender probe Stubborn 007 LE for Spiroplasma citri

<400> SEQUENCE: 131
aaccatcaag ttttatcccg ttt 23

<210> SEQ ID NO 132
<211> LENGTH: 22
<212> TYPE: DNA
<213> ORGANISM: Artificial Sequence
<220> FEATURE:
<223> OTHER INFORMATION: synthetic citrus stubborn disease target label extender probe Stubborn 008 LE for Spiroplasma citri

<400> SEQUENCE: 132
cctttgattg ttgccagttg tg 22

<210> SEQ ID NO 133
<211> LENGTH: 23
<212> TYPE: DNA
<213> ORGANISM: Artificial Sequence
<220> FEATURE:
<223> OTHER INFORMATION: synthetic citrus stubborn disease target label extender probe Stubborn 009 LE for Spiroplasma citri

<400> SEQUENCE: 133
ggatattgtc gtatccattt gct 23

<210> SEQ ID NO 134
<211> LENGTH: 27
<212> TYPE: DNA
<213> ORGANISM: Artificial Sequence
<220> FEATURE:
<223> OTHER INFORMATION: synthetic citrus stubborn disease target label extender probe Stubborn 010 LE for Spiroplasma citri

<400> SEQUENCE: 134
tgtttaattg actagcacta tacccac 27

<210> SEQ ID NO 135
<211> LENGTH: 20
<212> TYPE: DNA
<213> ORGANISM: Artificial Sequence
<220> FEATURE:
<223> OTHER INFORMATION: synthetic citrus stubborn disease target label extender probe Stubborn 011 LE for Spiroplasma citri

<400> SEQUENCE: 135
cgatcagcaa cagcactcgc 20

<210> SEQ ID NO 136
<211> LENGTH: 25
<212> TYPE: DNA
<213> ORGANISM: Artificial Sequence
<220> FEATURE:
<223> OTHER INFORMATION: synthetic citrus stubborn disease target label extender probe Stubborn 012 LE for Spiroplasma citri

<400> SEQUENCE: 136
tgacagttta ccattggttt taacc 25

<210> SEQ ID NO 137
<211> LENGTH: 19
<212> TYPE: DNA
<213> ORGANISM: Artificial Sequence
<220> FEATURE:
<223> OTHER INFORMATION: synthetic citrus stubborn disease target label extender probe Stubborn 013 LE for Spiroplasma citri

<400> SEQUENCE: 137
ttgtcaacgg ttcggttgc 19

<210> SEQ ID NO 138
<211> LENGTH: 23
<212> TYPE: DNA
<213> ORGANISM: Artificial Sequence
<220> FEATURE:
<223> OTHER INFORMATION: synthetic citrus stubborn disease target label extender probe Stubborn 014 LE for Spiroplasma citri

<400> SEQUENCE: 138
taactgctcg acaacttgct ctt 23

<210> SEQ ID NO 139
<211> LENGTH: 19
<212> TYPE: DNA
<213> ORGANISM: Artificial Sequence
<220> FEATURE:
<223> OTHER INFORMATION: synthetic citrus stubborn disease target label extender probe Stubborn 015 LE for Spiroplasma citri

<400> SEQUENCE: 139
cgcttggaat ttgcgtttt 19

<210> SEQ ID NO 140
<211> LENGTH: 28
<212> TYPE: DNA
<213> ORGANISM: Artificial Sequence
<220> FEATURE:
<223> OTHER INFORMATION: synthetic citrus stubborn disease target label extender probe Stubborn 016 LE for Spiroplasma citri

<400> SEQUENCE: 140
ttggtattta ccttatcaat tttgatat 28

<210> SEQ ID NO 141
<211> LENGTH: 29
<212> TYPE: DNA
<213> ORGANISM: Artificial Sequence
<220> FEATURE:
<223> OTHER INFORMATION: synthetic citrus stubborn disease target label extender probe Stubborn 017 LE for Spiroplasma citri

<400> SEQUENCE: 141
atttaacagt aatgtttact ttgtcattt 29

<210> SEQ ID NO 142
<211> LENGTH: 24
<212> TYPE: DNA
<213> ORGANISM: Artificial Sequence
<220> FEATURE:
<223> OTHER INFORMATION: synthetic citrus stubborn disease target label extender probe Stubborn 018 LE for Spiroplasma citri

<400> SEQUENCE: 142
attgttctga tgtcgcatta ttgt 24

<210> SEQ ID NO 143
<211> LENGTH: 31
<212> TYPE: DNA
<213> ORGANISM: Artificial Sequence
<220> FEATURE:
<223> OTHER INFORMATION: synthetic citrus stubborn disease target blocking probe Stubborn 019 BL for Spiroplasma citri

<400> SEQUENCE: 143
ccattatcag tatttcaata ttcttttatt t 31

<210> SEQ ID NO 144
<211> LENGTH: 27
<212> TYPE: DNA
<213> ORGANISM: Artificial Sequence
<220> FEATURE:
<223> OTHER INFORMATION: synthetic citrus stubborn disease target blocking probe Stubborn 020 BL for Spiroplasma citri

<400> SEQUENCE: 144
gtcaattttt actatctgca aaaagat 27

<210> SEQ ID NO 145
<211> LENGTH: 27
<212> TYPE: DNA
<213> ORGANISM: Artificial Sequence
<220> FEATURE:
<223> OTHER INFORMATION: synthetic citrus stubborn disease target blocking probe Stubborn 021 BL for Spiroplasma citri

<400> SEQUENCE: 145
aacgaaactt tatctttctc ataattg 27

<210> SEQ ID NO 146
<211> LENGTH: 27
<212> TYPE: DNA
<213> ORGANISM: Artificial Sequence
<220> FEATURE:
<223> OTHER INFORMATION: synthetic citrus stubborn disease target
blocking probe Stubborn 022 BL for Spiroplasma citri

<400> SEQUENCE: 146
ggtttaaact cactttggtt taaaaca 27

<210> SEQ ID NO 147
<211> LENGTH: 22
<212> TYPE: DNA
<213> ORGANISM: Artificial Sequence
<220> FEATURE:
<223> OTHER INFORMATION: synthetic housekeeping citrus gene Nad5 target
capture extender probe Nad 001 CE for NADH dehydrogenase internal
control

<400> SEQUENCE: 147
ggctatatga tctttgcttg cg 22

<210> SEQ ID NO 148
<211> LENGTH: 23
<212> TYPE: DNA
<213> ORGANISM: Artificial Sequence
<220> FEATURE:
<223> OTHER INFORMATION: synthetic housekeeping citrus gene Nad5 target
capture extender probe Nad 002 CE for NADH dehydrogenase internal
control

<400> SEQUENCE: 148
cgttttcatg atagcaaggt gct 23

<210> SEQ ID NO 149
<211> LENGTH: 24
<212> TYPE: DNA
<213> ORGANISM: Artificial Sequence
<220> FEATURE:
<223> OTHER INFORMATION: synthetic housekeeping citrus gene Nad5 target
capture extender probe Nad 003 CE for NADH dehydrogenase internal
control

<400> SEQUENCE: 149
cccctttatt tgaataccca ccta 24

<210> SEQ ID NO 150
<211> LENGTH: 21
<212> TYPE: DNA
<213> ORGANISM: Artificial Sequence
<220> FEATURE:
<223> OTHER INFORMATION: synthetic housekeeping citrus gene Nad5 target
capture extender probe Nad 004 CE for NADH dehydrogenase internal
control

<400> SEQUENCE: 150
gatgctatgg agggtcccac t 21

<210> SEQ ID NO 151
<211> LENGTH: 21
<212> TYPE: DNA
<213> ORGANISM: Artificial Sequence
<220> FEATURE:
<223> OTHER INFORMATION: synthetic housekeeping citrus gene Nad5 target
capture extender probe Nad 005 CE for NADH dehydrogenase internal -continued control

<400> SEQUENCE: 151
ggattgcata cttggtcacc c 21

<210> SEQ ID NO 152
<211> LENGTH: 28
<212> TYPE: DNA
<213> ORGANISM: Artificial Sequence
<220> FEATURE:
<223> OTHER INFORMATION: synthetic housekeeping citrus gene Nad5 target capture extender probe Nad 006 CE for NADH dehydrogenase internal control

<400> SEQUENCE: 152
caatatgaga tttaatgcca taactctt 28

<210> SEQ ID NO 153
<211> LENGTH: 23
<212> TYPE: DNA
<213> ORGANISM: Artificial Sequence
<220> FEATURE:
<223> OTHER INFORMATION: synthetic housekeeping citrus gene Nad5 target capture extender probe Nad 007 CE for NADH dehydrogenase internal control

<400> SEQUENCE: 153
cccagaaatt cttggatttc ttg 23

<210> SEQ ID NO 154
<211> LENGTH: 26
<212> TYPE: DNA
<213> ORGANISM: Artificial Sequence
<220> FEATURE:
<223> OTHER INFORMATION: synthetic housekeeping citrus gene Nad5 target label extender probe Nad 008 LE for NADH dehydrogenase internal control

<400> SEQUENCE: 154
tagcttattc aacttgcagt caatta 26

<210> SEQ ID NO 155
<211> LENGTH: 23
<212> TYPE: DNA
<213> ORGANISM: Artificial Sequence
<220> FEATURE:
<223> OTHER INFORMATION: synthetic housekeeping citrus gene Nad5 target label extender probe Nad 009 LE for NADH dehydrogenase internal control

<400> SEQUENCE: 155
tctttcactt aatgaatcac gcg 23

<210> SEQ ID NO 156
<211> LENGTH: 25
<212> TYPE: DNA
<213> ORGANISM: Artificial Sequence
<220> FEATURE:
<223> OTHER INFORMATION: synthetic housekeeping citrus gene Nad5 target label extender probe Nad 010 LE for NADH dehydrogenase internal control

<400> SEQUENCE: 156
ttacagaacg atctaaagag ggtca 25

<210> SEQ ID NO 157
<211> LENGTH: 19

<212> TYPE: DNA
<213> ORGANISM: Artificial Sequence
<220> FEATURE:
<223> OTHER INFORMATION: synthetic housekeeping citrus gene Nad5 target
label extender probe Nad 011 LE for NADH dehydrogenase internal
control

<400> SEQUENCE: 157
tgcggcaacc actggaata 19

<210> SEQ ID NO 158
<211> LENGTH: 22
<212> TYPE: DNA
<213> ORGANISM: Artificial Sequence
<220> FEATURE:
<223> OTHER INFORMATION: synthetic housekeeping citrus gene Nad5 target
label extender probe Nad 012 LE for NADH dehydrogenase internal
control

<400> SEQUENCE: 158
caggagctac gacgtcattc ct 22

<210> SEQ ID NO 159
<211> LENGTH: 20
<212> TYPE: DNA
<213> ORGANISM: Artificial Sequence
<220> FEATURE:
<223> OTHER INFORMATION: synthetic housekeeping citrus gene Nad5 target
label extender probe Nad 013 LE for NADH dehydrogenase internal
control

<400> SEQUENCE: 159
tttcgggccg ttttactctc 20

<210> SEQ ID NO 160
<211> LENGTH: 24
<212> TYPE: DNA
<213> ORGANISM: Artificial Sequence
<220> FEATURE:
<223> OTHER INFORMATION: synthetic housekeeping citrus gene Nad5 target
label extender probe Nad 014 LE for NADH dehydrogenase internal
control

<400> SEQUENCE: 160
gcatctctaa ctattcggtt agcg 24

<210> SEQ ID NO 161
<211> LENGTH: 23
<212> TYPE: DNA
<213> ORGANISM: Artificial Sequence
<220> FEATURE:
<223> OTHER INFORMATION: synthetic housekeeping citrus gene Nad5 target
label extender probe Nad 015 LE for NADH dehydrogenase internal
control

<400> SEQUENCE: 161
gcagctacta tggtaacagc tgg 23

<210> SEQ ID NO 162
<211> LENGTH: 21
<212> TYPE: DNA
<213> ORGANISM: Artificial Sequence
<220> FEATURE:
<223> OTHER INFORMATION: synthetic housekeeping citrus gene Nad5 target
label extender probe Nad 016 LE for NADH dehydrogenase internal
control

<400> SEQUENCE: 162
ccagtatccg cttcgattca t 21

<210> SEQ ID NO 163
<211> LENGTH: 25
<212> TYPE: DNA
<213> ORGANISM: Artificial Sequence
<220> FEATURE:
<223> OTHER INFORMATION: synthetic housekeeping citrus gene Nad5 target label extender probe Nad 017 LE for NADH dehydrogenase internal control

<400> SEQUENCE: 163
tttcaaacag tagacttttc aacca 25

<210> SEQ ID NO 164
<211> LENGTH: 21
<212> TYPE: DNA
<213> ORGANISM: Artificial Sequence
<220> FEATURE:
<223> OTHER INFORMATION: synthetic housekeeping citrus gene Nad5 target label extender probe Nad 018 LE for NADH dehydrogenase internal control

<400> SEQUENCE: 164
gttgggaaat cggcacagat a 21

<210> SEQ ID NO 165
<211> LENGTH: 27
<212> TYPE: DNA
<213> ORGANISM: Artificial Sequence
<220> FEATURE:
<223> OTHER INFORMATION: synthetic housekeeping citrus gene Nad5 target label extender probe Nad 019 LE for NADH dehydrogenase internal control

<400> SEQUENCE: 165
atttgtattt tactttttat tggtgct 27

<210> SEQ ID NO 166
<211> LENGTH: 24
<212> TYPE: DNA
<213> ORGANISM: Artificial Sequence
<220> FEATURE:
<223> OTHER INFORMATION: synthetic housekeeping citrus gene Nad5 target blocking probe Nad 0020 BL for NADH dehydrogenase internal control

<400> SEQUENCE: 166
cggctttgat tgttattact tctg 24

<210> SEQ ID NO 167
<211> LENGTH: 20
<212> TYPE: DNA
<213> ORGANISM: Artificial Sequence
<220> FEATURE:
<223> OTHER INFORMATION: synthetic housekeeping citrus gene Nad5 target blocking probe Nad 0021 BL for NADH dehydrogenase internal control
<220> FEATURE:
<223> OTHER INFORMATION: synthetic housekeeping citrus gene Nad5 target blocking probe Nad 0021 BL for NADH dehydrogenase internal control

<400> SEQUENCE: 167
tttttgctcg tgctagtgcc 20